United States Patent [19]

Garbers et al.

US005237051A

[11] Patent Number: 5,237,051

[45] Date of Patent: Aug. 17, 1993

[54] PURIFIED ENTEROTOXIN RECEPTOR PROTEIN

[75] Inventors: David L. Garbers; Stephanie Schulz, both of Dallas, Tex.

[73] Assignee: Vanderbilt University, Nashville, Tenn.

[21] Appl. No.: 623,033

[22] Filed: Dec. 6, 1990

[51] Int. Cl.$^5$ ..................... C07K 13/00; C12N 15/12
[52] U.S. Cl. ................... 530/350; 435/69.1; 435/370.1
[58] Field of Search ............ 530/350; 435/69.1, 252.3, 435/320.1; 436/501

[56] References Cited

PUBLICATIONS

Cell. vol. 63, pp. 941-948, Nov. 30, 1990, Schulz et al. Guanylyl Cyclase is a Heat-stable Enterotoxin Receptor.

J. Biol. Chem. 261 (3) pp. 1470-1476, Jan. 25, 1986, Kuno et al. Characterization of the Receptor for Heat-Stable Enterotoxin from *Escherichia coli* Cell in Rat Intestines.

*Primary Examiner*—Robert J. Hill, Jr.
*Assistant Examiner*—John D. Ulm
*Attorney, Agent, or Firm*—Reising, Ethington, Barnard, Perry & Milton

[57] ABSTRACT

RNA has been cloned for the intestinal receptor which recognizes heat stable enterotoxins and has guanylyl cylase activity. The protein sequence has been deduced. The protein has been expressed in cultured cells. Data shows that the protein binds enterotoxin and signals normally through the cyclic GMP second messenger system.

2 Claims, 13 Drawing Sheets

Fig-1A

```
GCCTGAAGATTGTTCTGGTACCTCAAGCGCTCAGAGGCTGGGGTGTCCTATTTTTCTGAGGTGCTCAGCTTCAGGAAGGATGTATTGAGACGCAGTGAACA
 P  E  D  [G] F  W  Y  L  N  A  L  E  A  G  V  S  Y  F  S  E  V  L  S  F  K  D  V  L  R  R  S  E  Q

GTTCCAGGAAATCCTAATGGG       225
 F  Q  E  I  L  M  G       075

CCGTAACAGGAAGAGCAATGTGATTGTTATGTGTGG[C]GTACACGCCAGAAACCTTCTACAATGTGAAAGGTGACCTCAAAGTGGCTGACGACACTGTTGTCAT
 R  N  R  K  S  N  V  I  V  M  [G] T  P  E  T  F  Y  N  V  K  G  D  L  K  V  A  D  D  T  V  V  I

CCTGGTAGATCTGTTCAGTAA       545
 L  V  D  L  F  S  N       255

CCATTACTTTGAGGATGACACCAGAGCTCCTGAGTATATGGACAATGTCCTCGTCCTGACACTGCCTCCTGAAAAGTTCATCGCAAACGCCTCTGTCTC
 H  Y  F  E  D  D  T  R  A  P  E  Y  M  D  N  V  L  V  L  T  L  P  P  E  K  F  I  A  N  A  S  V  S

TGGGAGTTTCCATCGGAAAG       752
 G  R  F  P  S  E  R       235

AAGGACTTTCTCTCGGCTTACTTGGAGGGGACCTTGCTCTTGTTTGGACACATGCTGCAGACGTTTCTTGAAAATGGAGAATCTGTCACCACGCCCAAGTT
 S  D  F  S  L  A  Y  L  E  G  T  L  L  L  F  G  H  M  L  Q  T  F  L  E  N  G  E  S  V  T  P  K  F

CGCTCGTGCGTTCAGGAATCT       785
 A  R  A  F  R  N  L       395

CACTTTCAAGGCTTAGAGGGGCCCGTGACTCTGGATGACAGTGGGGACATTGACAACATTATGTGTCTTCTGTATGTGTCTCTGGATACCAGGAAATA
 T  F  Q  G  L  E  G  P  V  T  L  D  D  S  G  D  I  D  N  I  M  [G] L  L  Y  V  S  L  D  T  R  K  Y
 T

CAAGGTTCTTATGGCGTATGA       222
 K  V  L  M  A  Y  D       075
```

```
TGACATTGCTAAGGGGATGTCCTATCTGCACTCCAGTAAGATTGAAGTCCACCAACTGCGTGGTGGACAGTCGCATGGTG
 D   I   A   K   G   M   S   Y   L   H   S   S   K   I   E   V   H   G   R   L   K   S   T   N   C   V   V   D   S   R   M   V

GTGAAGATCACTGATTTGGGGTG
 V   K   I   T   D   F   G   C

CAATTCCATCCTGCCTCCAAAGAAAGACCTGTGGACTGCCCCCGAGCACCTGCGCCAAGCTACTATCTCTCAGAAAGGAGAGCTGTACAGCTTCAGC
 N   S   I   L   P   P   K   K   D   L   W   T   A   P   E   H   L   R   Q   A   T   I   S   Q   K   G   E   L   Y   S   F   S

ATCATTGCCCAGGAGATCATCCT
 I   I   A   Q   E   I   I   L

CCGCAAGGAAACTTTCTACACGCTGAGCTGCCGGGATCAGAATGAGAAGATTTTCAGAGTGGAAAATTCCTATGGACGAAACCCTTCCGCCCAGAT
 R   K   E   T   F   Y   T   L   S   C   R   D   Q   N   E   K   I   F   R   V   E   N   S   Y   G   T   K   P   F   R   P   D

CTCTTCCTGGAAACCGCAGATGA
 L   F   L   E   T   A   D   E

GAAGGAGCTGGAGGTCTATCTATTGGTCAAAAGCTGTTGGGAGGAGGATCCAGAAAAGAGACCCAGATTTCAAGAAAATCGAGAGCACTAGCCAAG
 K   E   L   E   V   Y   L   L   V   K   S   C   W   E   E   D   P   E   K   R   P   D   F   K   K   I   E   S   T   L   A   K

ATATTTGGCCCTTTTTCATGACCA
 I   F   G   L   F   H   D   Q

AAAAAATGAATCTTACATGGACACCTGATCCGACGTCTACAGCTGTATTCTCGGAACCTGGAGCACCTGGTGGAGGAAAGGACTCAGCTGTACAAG
 K   N   E   S   Y   M   D   T   L   I   R   R   L   Q   L   Y   S   R   N   L   E   H   L   V   E   E   R   T   Q   L   Y   K

GCCGAGAGGGACAGGGCTGACCA
 A   E   R   D   R   A   D   H
```

```
GC-A  SDLTAVYLFLTNTSYPISAARVGPAVELALARVKARPDLLPGWTVRMVLQSSENAAGVESDTAAPLAAVDLK
GC-B  RNILAVYLPEHMLSYAAAHPRVQPAVALAVEAL·GRA··LR···MDLRFVSBE·LDQAESEYLAPLRAVDLK
GC-C                         SQVRQKCHNGTYEISVLMMDNSAYKEPLONLRDAVEEGLDIVRKALREAELNV

GC-A  WERSPAV    80
GC-B  LYHDPDL    74
GC-C  TVNATFI    60

GC-A  FLGPGCVYSAAPVGRFTAHVRVPLLTAGAPALGIVKDE·MALTTRTGPSHVKLGDFYTALTRRLGMEHQALV
GC-B  LGPGCVYFAASMARFASHNHEPLLTAGAVASGFAAKNEHYRTLVRTGPSAPKLGEFVTLIGHFNMTARIAAL
GC-C  YSDGLIHKSGDCRSSTCEQLDLREITRDRKMGCVLMGPSCTYSTFQMYLDTELNYPMISAGSFGLSCDYKET

GC-A  LYADRLQ    159
GC-B  CVLDART    154
GC-C  TRILPP     140

GC-A  DDRPCFFIVEGLYMRVRERLNITMNHQEFMEGDDDHYPKLLRAVRKQRVIYIVICSSPDAFRNLMELALNAGLT
GC-B  DDRPHYFTIEGVFEALQGS·NLSMQHQVMTR·EPGQPEQATHFIRANGRIVICGPLEMLHEILEAQRENLT
GC-C  ARKLMYFLMDFWKVNNAPF·KTFSWNSSYVY·KNGSEPEDCFWYLNALEAGVSYFSEVLSFKDVFRRSEQFQE

GC-A  GEDYVFF    239
GC-B  NGDYVEF    232
GC-C  ILMGRNR    218
```

*Fig-3A*

```
GC-A    HLDVFGQSLKSAGGLVPQKPW..ERGDGQDRSARQAFQAAKITYKEPDNPEYLEFLKQLKLADKF.NFTM
GC-B    YLDVFGESLRAGPTRATGRPWQDNRTQEQAQALPEAFQTVLVLTYREPPNPEYQEFQNRELIRAREDF.GVEL
GC-C    KSNVIVMCGTPETFYNVKGQLKVADDTVVILVDLFSNHYFEDDI...APEYMDNVLVLTPPEKFIANASV

GC-A    EDQL...                                                              313
GC-B    APSL...                                                              308
GC-C    SGRFPSE                                                              294

GC-A    KNIPASFHDGLLYAVTETLIAQGGTVTDGENITQRMWNRSFQGVTGYLKIDRNGDRDTDFSWDM.DPET
GC-B    MNLIAGCFYDGILLYAQVLNETIQEGGTREDGLRIVEKMQGRYHGVTGLMVMDKNDRETDFVLWAMGDLES
GC-C    RSDFSLAYLEGTLLFGHMLQTFLENGESVITP.KFARAFRNLTFQGLEGPVTLDDSGDNIMCLYVSLDTR

GC-A    GAFRVVL                                                              392
GC-B    GDFQPAA                                                              388
GC-C    KYKVLMA                                                              373

GC-A    MYNGTSQELMAVSEHKLYMPLGYPPPDVPKCGFQNEDPACNQDHFSTLEVLALVGSLSLISFLIVSFFIYRKM
GC-B    HYSGAEKQIWWTG.RPIPMVKGAPPLQNPPCAFDLDDPSDKTPLSTLAIVALMFGVSSFLJFRKL
GC-C    YDTHKNQTPVATSPNFIWKNHRLPNDVP.G......GPQILMQAVFTLTGIVVVLIALLVLRKY

GC-A    QLEKELV                                                              472
GC-B    MLEKELA                                                              467
GC-C    RRDHELR                                                              441
```

Fig-3B

```
GC-A  SELWR.VRWEDLQPSSLERHLRSAGSRTTLSGRQSNYQSLLTEGQFQVFAKTANYKGNLVAVKRVNRKRIEL
GC-B  SMLWR.IRWEELQPSSLERHLRSAGSRTTLSGRQSSYGSLMRQSSYGSLMRQSSYHKGAGSRTTLSLRQSSYGSLMRQSSYHKGNVVAIKHFKGNVVAIKHVNKKRIEL
GC-C  QKKMSHIPSGNIFP..LETNETNHVSLKIDDDR......RRDTIQRVRQCKYDKKVI-LKDLKHCDGNF

TRKVLFE  551
      TRQVLFE  546
      SEMQKIE  512

GC-A  LKHMRDVQNEHLTRFVGACTDPPNICILTEYCPRGSLQDILENE......SITLDWMFRYSLTNDIVKGMLFLH
GC-B  LKHMRDVQFNHLTRFIGACIDPPNICIVTEYCPRGSLQDILEND......SINLDWMFRYSLINDLVKGMAFLH
GC-C  LNKLLQSDYYNLTKFYGTVKLDTRLFGVVEYCERGSLREVLNDTISYPDGTFMDWEFKISVLNDIAKGMSYLH

NGAICSH   626
      NSIISSH   621
      SSKIEVH   592

GC-A  GNLKSSNCVVDGRFVLKITDYGLESFR.DPEPEQGHTLFAKK.LWTAPELLRMAISPPARGSQAGDVYSFGIIL
GC-B  GSLKSSNCVVDSRFVLKITDYGLASFRSTAEPDDSHALYAKK.LWTAPELLISGNPLPTTGMKADVYSFAIIL
GC-C  GRLKSTNCVVDSRMVKITDFGCNSII......LPPKKDLWTAPEFLRQATISQKG....ELYSFSIIA

QEIALRS   704
      QEIALRS   700
      QEILRK    657
```

*Fig-3C*

```
GC-A   GVFYVEGLDLSPKEIERVTRG·EQPPFRPSMDLQSHLE·ELG··QLMQRCWAEDPQERPPFQQIRLARK··
GC-B   GPFYLEGLDLSPKEIERVTRG·QRPYFRPSIDRTQLNE·ELV··LLMERCWAQDPTERPDFGQIKGFIRR··
GC-C   ETFYTLSCR·DQNEKIFRVENSYGTKPFRPDLFLETADEKELEVYLLVKSCWEEDPEKRPDFKKIESTLAKIF

GC-A   ··FNKEN   776
GC-B   ··FNKEG   772
GC-C   GLFHDQK   736

GC-A   SSNILDNLLSRMEQYANNLEELVEERTQAYLEEKRKAEALLYQILPHSVAEQLKRGETVQAEAFDSVTIYFSD
GC-B   GTSILDNLLLRMEQYANNLEKLVEERTQAYLEEKRKAEALLYQILPHSVAEQLKRGETVQAEAFDSVTIYFSD
GC-C   NESYMQTLIRRLQLYSRNLEHLVEERTQLMKAEFDRADHLNFMLLPRLVVKSLKEKGIVEPELYEEVTIYFSD

GC-A   IVGFTAL   856
GC-B   IVGFTAL   852
GC-C   IVGFTI    816

GC-A   SAESTPMQVVTLLNDLYTCFDAVIDNFDVYKVETIGDAYMVVSGLPVRNGQLHAREVARMALALLDAVRSFRI
GC-B   SAESTPMQVVTLLNDLYTCFDAIIDNFDVYKVETIGDAYMVVSGLPGRNGQRHAPEIARMALALLDAVSSFRI
GC-C   CKYSTPMEVVDMLNDIIVKSFDQIHHDVYKVETIGDAYMVVDILSKMALDILSFMGTFEL

GC-A   RHRPQEQ   936
GC-B   RHRPHDQ   932
GC-C   EHLPGLP   896
```

Fig-3D

```
GC-A   LRLRIGIHTGPVCAGVVGLKMPRYCLFGDTYNTASRMESNGEALKIHLSSETKAVLEEFDG·FEKELRGDVEM
GC-B   LRLRIQVHTGPVCAGVVGLKMPRYCLFGDTYNTASRMESNGQALKIHVSSTTKDALDELGC·FQLELRGDVEM
GC-C   VWIRIGVHSGPCAAGVVGLIKMPRYCLFGDTYNTASRMESTGLPLRIHMSSSTIAILRRTDQQFLYEVRGETYL

GC-A   KGKGKVR       1015
GC-B   KGKGKMR       1011
GC-C   KGRGTET        976

GC-A   TYWLLGERGCSTRG
GC-B   TYWLLGERKGPPGEL
GC-C   TYMLTGMKDQEYNLPTPPTVENQQRLQTEFSDMIVSALQKRQASGVKSRRPTRVASYKKGFLEYMQLNNSDHD

GC-A                 1029
GC-B                 1026
GC-C   STYF          1053
```

Fig-3E

PURIFIED ENTEROTOXIN RECEPTOR PROTEIN

TECHNICAL FIELD

The present invention relates to the cloning and use of an enterotoxin receptor. More specifically, the present invention relates to the specific protein, the clone encoding the protein, the peptide portion of the protein having receptor binding activity, and the DNA sequence encoding the protein. The protein and its uses relate to the control of diarrhea as well as the molecular mechanism thereof.

BACKGROUND OF THE INVENTION

Diarrhea can be caused by small, heat stable peptide toxins (ST) produced by various pathogenic bacteria (1). In developing countries, such toxins may be responsible for 50% to 80% of the reported cases of diarrhea (2). ST are also a major cause of diarrhea in laboratory and domestic animals (3). Thus, it can be concluded that it is desirable to be able to control diarrhea by understanding the mechanism of action of ST, and more specifically, controlling diarrhea by affecting that mechanism.

It has been previously determined that heat stable enterotoxins bind to a cell surface receptor in the intestine which subsequently leads to an activation of guanylyl cyclase (4,5). The rise in cyclic GMP then stimulates fluid secretion thereby causing diarrhea.

Previous reports have concluded that the ST receptor is a distinctly different protein than quanylyl cyclase based on partial chromatographic separation of a detergent-solublized ST-binding protein from guanylyl cyclase activity (6,7). However, the ST binding and cyclase activities were not completely resolved by these studies. Further, the detergent solublized binding protein representing a functional receptor was not fully demonstrated in these studies.

Previous studies have shown that plasma membrane forms of guanylyl cylase can serve as cell-surface receptors for various peptides (8,9). Two distinct forms of plasma membrane guanylyl cylase designated as GC-A and GC-B have been isolated from various mammalian tissues and shown to bind natriuretic peptides (10,11,12,13).

The inventors of the present invention have significantly furthered the research relating to the ST receptor in combination with the research relating to plasma membrane forms of guanylyl cylase by identifying a unique, apparently intestinal specific guanylyl cylase designated as GC-C by the inventors. The inventors show herein the ability of this discovery to be utilized in the field of therapeutics, receptor detection, and ligand detection.

SUMMARY OF THE INVENTION

In accordance with the present invention, there is provided a protein having a biological property of binding heat stable enterotoxin and having guanylyl cylase activity.

The present invention further provides a method of expressing enzyme activity in a cell line, the method including the steps of expressing a clone in cells which encodes for a guanylyl cylase for heat stable enterotoxin and increasing guanylyl cylase activity in the cells.

The invention further provides a purified and isolated DNA sequence consisting essentially of a DNA sequence encoding a polypeptide having the biological property of binding heat stable enterotoxin.

Also in accordance with the present invention is an assay method for detecting enterotoxin receptor binding ligand in a fluid sample. The method includes the steps of exposing cultured cells, having incorporated therein a clone capable of encoding for a guanylyl cylase receptor for heat stable enterotoxin, to the fluid sample and detecting an elevation in guanylyl cylase activity as an indication of the presence of ligand in the sample.

Further, the present invention provides a vector comprising a nucleotide sequence encoding for a polypeptide having a biological property of binding heat stable enterotoxin.

The present invention further provides a method for detecting enterotoxin receptor binding ligand in a fluid sample including the steps of exposing cultured cells, having incorporated therein a clone capable of encoding for and overproducing a guanylyl cylase receptor for heat stable enterotoxin, to the fluid sample under competitive binding conditions with labeled ligand and detecting the binding of the labeled ligand as a measure of the presence of ligand in the fluid sample.

Finally, the present invention provides a method of expressing a receptor in cells including the steps of incorporating a DNA sequence encoding a polypeptide having a biological property of binding heat stable toxin in the cell's genome and over-expressing the polypeptide.

FIGURES IN THE DRAWINGS

Other advantages of the present invention will be readily appreciated as the same becomes better understood by reference to the following detailed description when considered in connection with the accompanying drawings wherein:

Figure 1A:
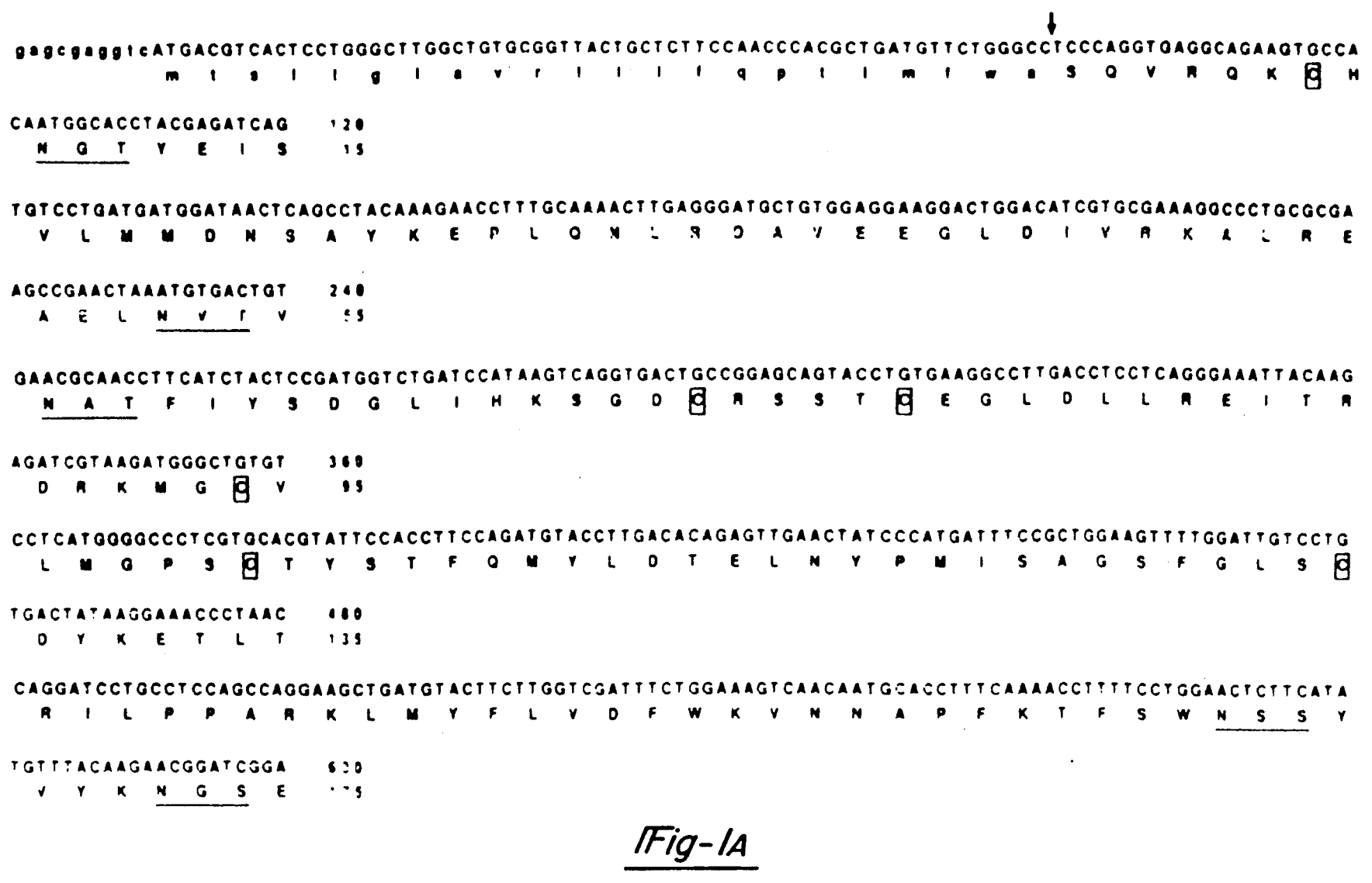
Figure 1C:
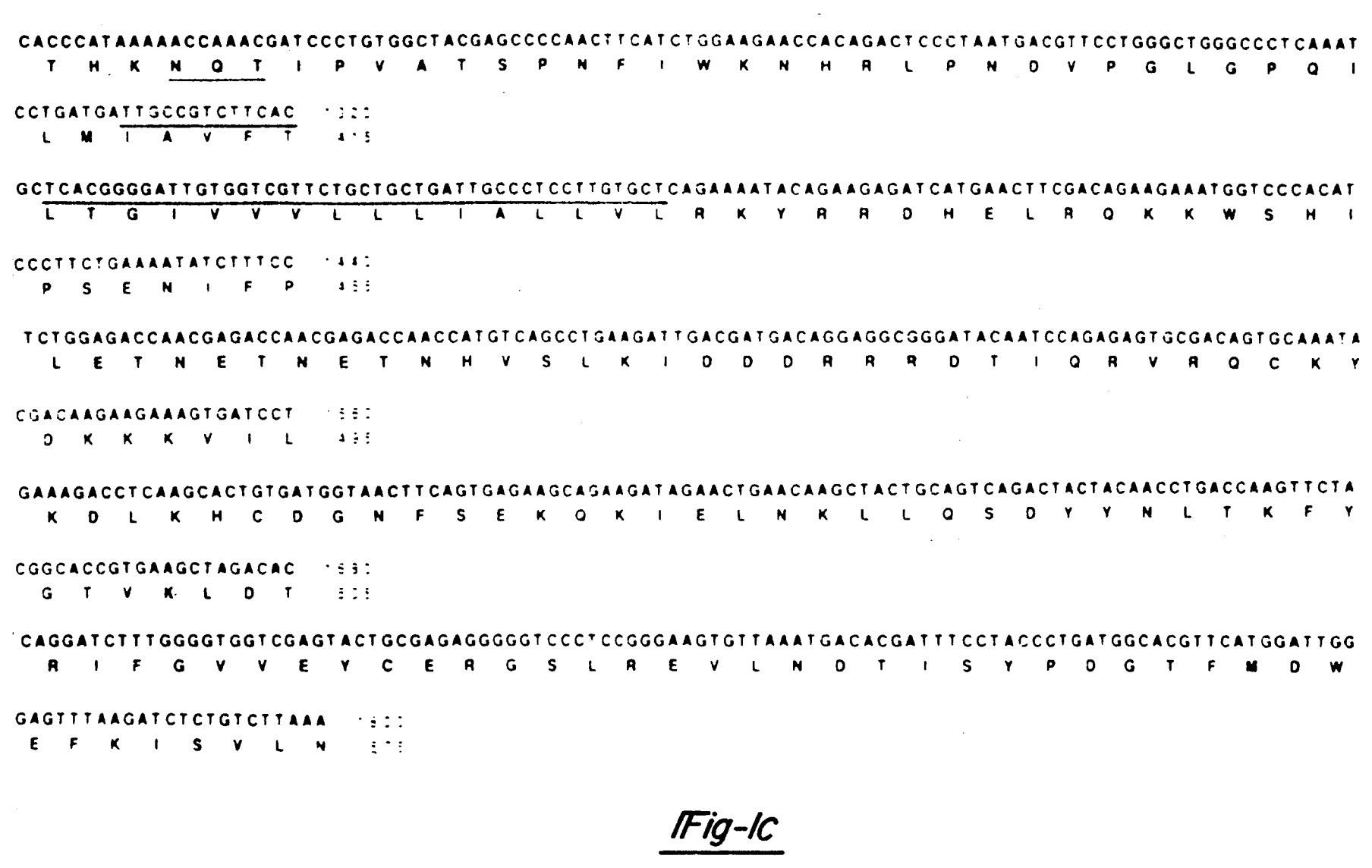
Figure 1E:
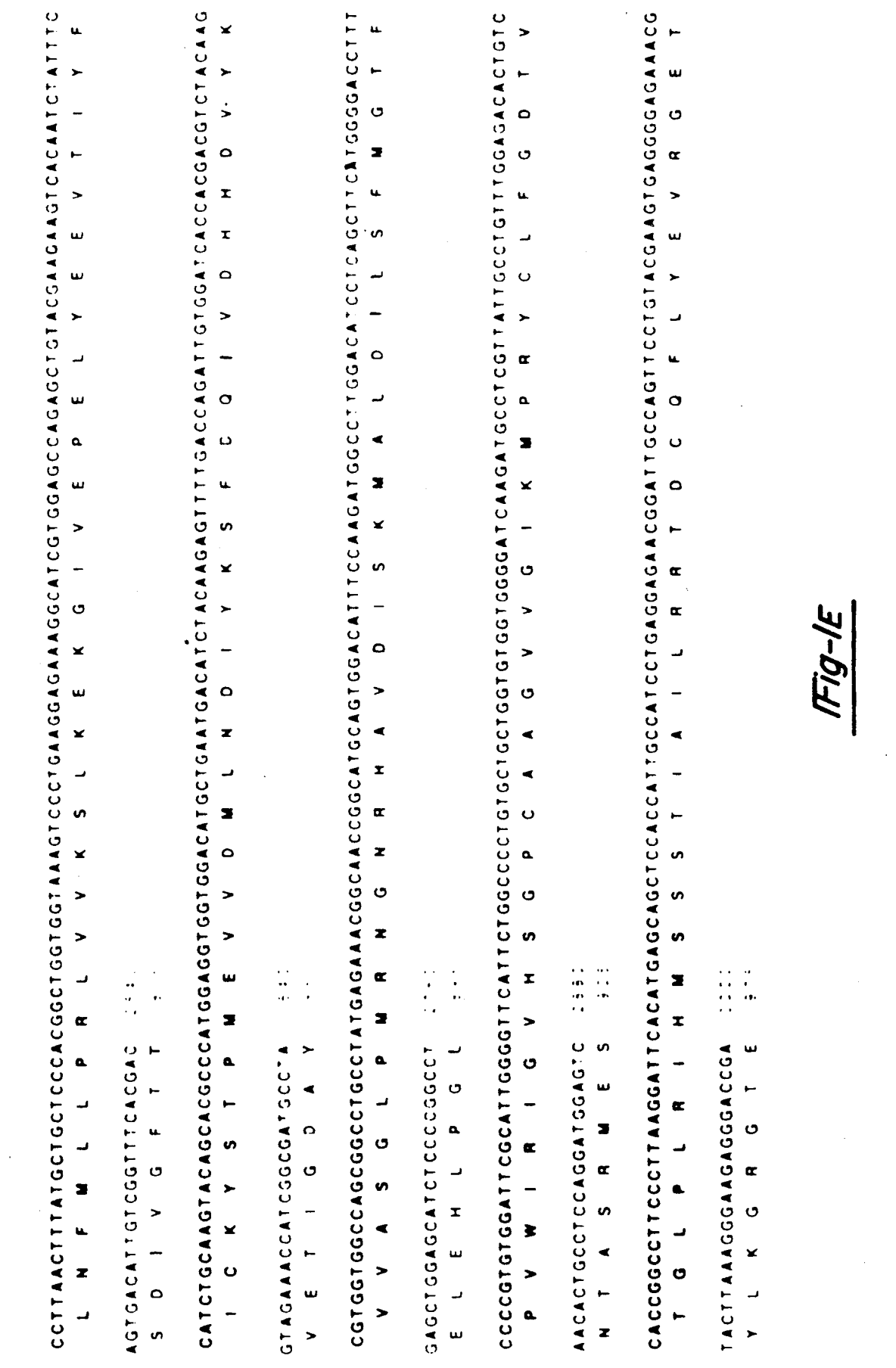
Figure 1F:
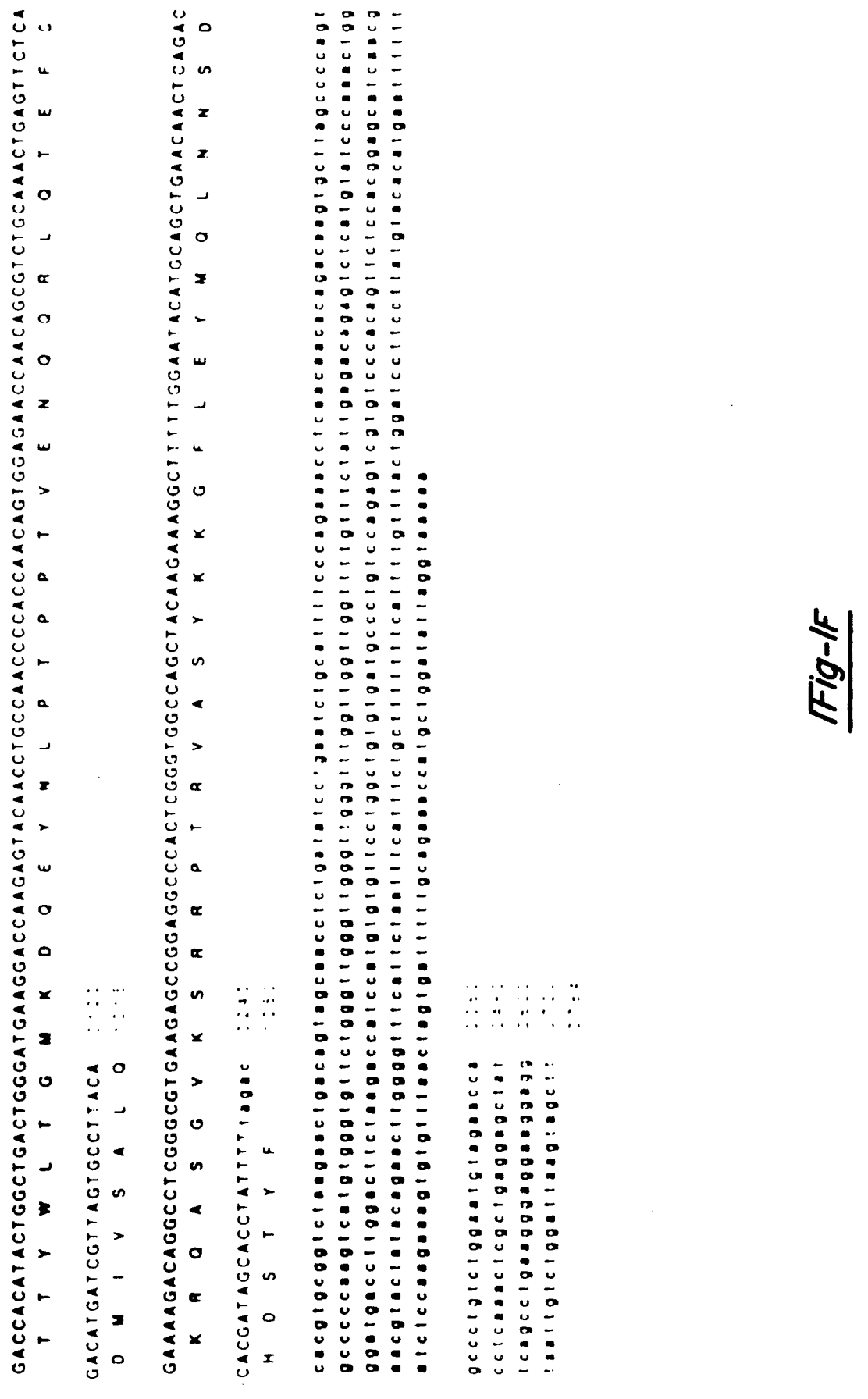

FIG. 1 shows the nucleotide and the deduced amino acid sequence of GC-C, amino acid being numbered beginning at the predicted signal cleavage site, the transmembrane being demarcated by bold overline, cycsteine residues being boxed, and potential N-linked glycosylation sites being underlined;

FIG. 3 shows the amino acid sequence comparison of GC-A, GC-B, and GC-C;

DETAILED DESCRIPTION OF THE INVENTION

Figure 2:
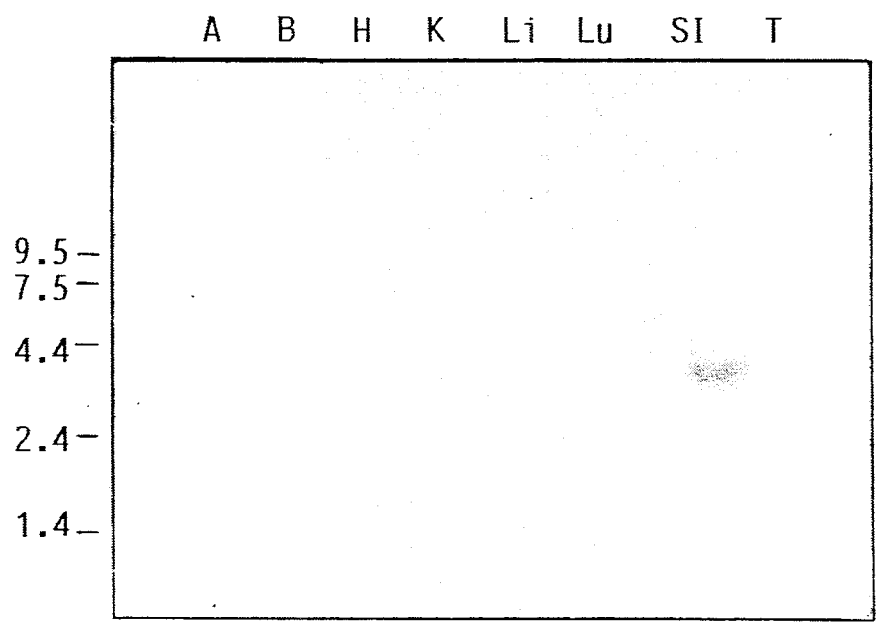
FIG. 2 is a photo-microradiograph showing the Northern Blot Analysis of GC-C steady state RNA levels.

Using the polymerase chain reaction (PCR), a unique, apparently intestinal-specific guanylyl cyclase (GC-C) has been identified. This protein has a biological property of binding heat stable enterotoxin and further has guanylyl cylase activity. Accordingly, the protein includes a polypeptide sequence having a biological property of binding heat stable enterotoxin as well as a polypeptide sequence having guanylyl cylase activity and being capable of causing cells to increase guanylyl cylase activity in the presence of enterotoxin. The areas of the sequence have been identified as set forth below.

The following experimental results show that the isolated protein has a general structure substantially similar to previously developed models for plasma membrane forms of the enzyme.

As evidenced below, applicant has isolated the DNA sequence which includes portions encoding for the polypeptide having the biological property of binding heat stable enterotoxin as well as the polypeptide having guanylyl cylase activity. Applicant has constructed a vector comprising the nucleotide sequence encoding for the enzyme including both of the aforementioned polypeptides and has found that the expressed protein does not bind natriuretic peptides, but specifically binds an *Escherichia coli* ST. Applicant has also found that ST also markedly stimulates the accumulation of cyclic GMP in mammalian cells expressing GC-C. It can therefore be concluded that an intestinal guanylyl cylase serves as a cell surface receptor for the heat stable enterotoxins which has been isolated through cloning. The receptor is unique in that it is the first isolated receptor protein having the property of being capable of binding the heat stable enterotoxin coupled to the guanylyl cylase activity. As an endogenous ligand is hypothesized, it is expected that the receptor can be used as a therapeutic to control intestinal fluid permeation, as well as abnormal conditions caused by bacterially released enterotoxin.

MATERIALS AND METHODS

Amplification of Small Intestinal Guanylyl Cylases

The novel GC-C was isolated by the following method. Degenerate oligonucleotide primers were designed based on two regions of the amino acid sequence conserved in the catalytic domains of the membrane and soluble guanylyl cyclases thus far cloned. These amino acid sequences are not conserved in either of the two putative intracellular domains of bovine brain adenylyl cyclase (14). The sense and anti-sense primers corresponded to amino acids 886–896 and 957–965 of GC-A, respectively (10). Each primer had restriction endonuclease recognition sites added to the 5′ end to aid in subcloning amplified products. The polymerase chain reaction (PCR) was performed using template cDNA prepared from rat small intestinal mucosa poly(A) RNA. Approximately 50 ng template cDNA were amplified using the GeneAmp DNA Amplification reagent kit (US Biochemical Corp.) with degenerate primers at a final concentration of 1 uM. An amplified product of the expected size (−250 bp) was obtained, and 1% of this product was reamplified under the same conditions. Following agarose gel purification, the amplified product was digested with restriction enzymes recognizing sequences introduced by the primers and was then ligated to compatible M13 sequencing vectors. Recombinant phage were sequenced. In addition to CG-A and GC-B, a unique guanylyl cylase-like sequence was obtained. This sequence, designated SIM3, was used as a probe to screen a rat small intestine cDNA library.

Cloning and Sequencing of GC-C

RNA was prepared from rat small intestine by the guanidinium thiocyanate/LiCl precipitation method (15). Poly(A) RNA was selected, and oligo(dT)-primed cDNA prepared using Superscript MMLV reverse transcriptase (Bethesda Research Labs). cDNA greater than 2 kb in length was selected by agarose gel electrophoresis, ligated to gtll phage arms and packaged. $1\times10^6$ independent recombinant plaques were screened using SIM3 as a probe. Filters were prehybridized at 42° C. in a solution containing 5 X SSC (IX is 0.15 M NaCl, 15 mM Na citrate, pH 7.0), 5 X Denhardt's (1 X is 0.2% BSA, 0.2% Ficoll, 0.2% polyvinylpyrrolidone), 0.25% SDS, 100 ug/ml denatured salmon sperm DNA, and hybridized in the same solution containing 20% formamide and 20 mM $NaH_2P)_4$ but without SDS. PCR amplified probe, labeled by random-priming, was added at $1\times10^6$ cpm/ml. Filters were washed at room temperature and twice at 60° C. in IX SSC/0.1% SDS and exposed overnight at 70° C. to Kodak X-OMat AR film.

DNA was prepared from purified positive phage clones, and cDNA inserts excised with EcoRl. The largest insert (3.8 kb), designated GC-C was cloned into Bluescript (Stratagene), and sequenced by subcloning restriction fragments into M13 mp18 and 19 sequencing vectors.

Northern blotting was performed (13). The blot was probed with the 5′ Sacl fragment of GC-C (nucleotides 1-868), and washed at 65° C. in 0.1 X SSC/0.1% SDS. Exposure was at −70° C. for 1 week.

Expression of Cloned GC-C

The complete nucleotide sequence of GC-C was excised from Bluescript with Xhol and Smal, and ligated to the mammalian expression vector pSVL (Pharmacia). 100 mm plates of COS-7 cells, maintained in Dulbecco's Modified Essential Medium (DMEM)/10% calf serum, were transfected with 5 ug of the expression construct (pSVL-C) or with vector alone using the DEAE-dextran method (16). For binding and stimulation assays, cells were plated 24 hours after transfection ($-5\times10^5$ cells/plate). Assays were performed 48–72 hours after transfection.

Guanylyl Cyclase and Cell Stimulation Assays

Membranes were prepared from transfected cells as previously described (13). Fifty ug solubilized membrane protein were incubated for 10 minutes at 30° C. in a total volume of 0.15 ml containing 20 mM N-2-hydroxyethylpiperizine-$N^1$-2-ethanesulfonic acid HEPES (pH 7.4), 1 mM $MnCl_2$, 0.2 mM 3-isobutyl-1-methylxanthine (IBMX), 0.1 mM GTP and 1 uCi [a-$^{32}$P]GTP. Reactions were stopped with 0.6 ml 30 mM Zn acetate and 0.5 ml 36 mM $Na_2CO_3$. [$^{32}$P]Cyclic GMP was purified by alumina column chromatography and quantified in a Beckman LS-7000 liquid scintillation counter.

Intracellular levels of cyclic GMP were measured as previously described (13). Transfected cell monolayers in 35 mm plates were washed with serum-free medium and preincubated at 37° C. in medium containing 0.1 mM IBMX. Cells were then incubated for 10 minutes in 0.5 ml fresh medium/0.1 mM IBMX containing various concentrations of STa (an 18 amino acid *E. coli*- derived heat-stable enterotoxin) or natriuretic peptide. Stimulated cells were extracted with perchloric acid, and cyclic GMP in the extract determined by radioimmunoassay following purification by Dowex/alumina chromatography (17).

Binding Assay

STa was radioiodinated to a specific activity of approximately 1300 Ci/mmole using Enzymobeads (BioRad). $^{125}$I-4TyrST was separated from $^{125}$I-18TyrST and from unlabeled toxin by high pressure liquid chromatography (18). Transfected cells were washed twice with serum-free medium containing 0.1% bovine serum albumin (BSA), then incubated for one hour at room temperature in 0.5 ml serum-free medium/0.1% BSA containing 1 uCi $^{125}$I-STa (final concentration approximately 1 nm) plus various concentrations of cold STa. Following the incubation, the medium was aspirated and the cell monolayers washed five times with Hanks Balanced Salt solution/0.1% BSA. cells were removed from the plate with trypsin/EDTA, and associated $^{125}$I-STa determined in a Beckman Gamma 7000. Results are expressed as the percentage of specific binding.

Results of Experimentation

Degenerate oligonucleotide primers based on conserved sequences in both the soluble and plasma membrane forms of the guanylyl cyclase enzyme were used to amplify template cDNA prepared from small intestine mucosa in order to obtain and purify new members of the guanylyl cyclase enzyme family. The results included not only the known GC-A and GC-B receptors but also the novel guanylyl cyclase like sequence GC-C. The PCR generated sequence, SIM3, was used as a probe to screen a small intestine cDNA library. This screening process resulted in the detection of a number of clones that hybridized to the probe under moderately stringent washing conditions of 1 x SSC at 60° C.

The partial sequencing of a number of these clones suggested that they were identical and therefore the longest cDNA insert, identified as clone 11a, was selected for further study. When the region of the clone 11a corresponding to the region flanked by the degenerated primers was sequenced, it was determined that clone 11a was not the cDNA that corresponded to SIM3 even though it was another member of the guanylyl cyclase family. In other words, the sequence indicated that a novel, not before identified, cyclase was isolated. The inventors of the present invention have not yet isolated the cDNA clone that would encode the SIM3 sequence, but it is very likely it encodes another form of the guanylyl cyclase.

As shown in FIG. 1, valine (TGT) is substituted for the methionine (ATG) found in other guanylyl cyclases at the 3' end of the sequence corresponding to the sense primer, at amino acids 867–878. This nucleotide change can reduce amplification of this sequence with the degenerate primers chosen (19) and can explain the failure to amplify the sequence of clone 11a (GC-C) from small intestine cDNA.

As stated above, the nucleotide and induced amino acid sequences of GC-C are shown in FIG. 1. With specific regard to the sequencing, the 3784 bp nucleotide sequence includes an open reading frame of 3225 bp following the first ATG. Only 10 bp precede the putative initiation codon, but the occurrence of this ATG within the context of an appropriate consensus sequence (20), and an apparent signal peptide immediate to it suggest that it is the true initiation codon. Cleavage of the 22 residue signal peptide (21) would result in a mature unprocessed protein of approximately 121 Kda. Hydrophobic analysis predicts a single transmembrane domain. The extracelluar portion of the encoded protein contains eight potential N-linked glycosylation sites and nine cysteine residues. The intracellular domain contains both the protein kinase-like and guanylyl cyclase catalytic domains normally seen in the plasma membrane forms of the enzyme. Following the catalytic domain, GC-C has an extended carboxyl tail, rich in uncharged polar amino acids (20% of the terminal 70 residues are Q or S). The function of this domain is not known, and it does not coincide with any sequence currently in the protein data base.

It has been reported by others that guanylyl cyclase activity in small intestinal mucosa is difficult to solubilize with non-ionic detergents, and it has been proposed that this form of the enzyme is linked to cytoskeletal elements (7). If true, then the carboxyl tail of GC-C, not found in other plasma membrane guanylyl cyclase, may anchor the enzyme to the cytoskeleton in epithelial cells.

As shown in FIG. 2, Northern blot analysis demonstrates that small intestine is the primary site of transcription of the 4 kb mRNA encoding GC-C. However, Northern analysis using total cellular RNA is an insensitive method for detecting rare messages or messages expressed in a limited number of cell types within an organ. The possibility exists, therefore, that GC-C is expressed at low levels in additional tissues.

Primary Sequence Comparisons

A comparison of the amino acid sequence of GC-C with the amino acid sequences of the natriuretic peptide receptors, GC-A (22) and GC-B (13), is shown in FIG. 3. For purposes of comparison, three domains can be considered: the extracellular binding domain, and the intracellular protein kinase-like and guanylyl cyclase catalytic domains.

While the binding domains of GC-A and GC-B are fairly similar (43% identical), reflecting their ability to bind a variety of natriuretic peptides, the extracellular domain of GC-C is quite unlike that of either of these forms (10% identical to GC-A or GC-B). This suggests that the endogenous ligand for this receptor is unlike the natriuretic peptides. That is, the inventors of the present invention isolated a novel protein having a novel binding domain. The extracellular domain of GC-C also bears no resemblance to the sea urchin guanylyl cyclase extracellular domains (23,24). The protein kinase-like domain of GC-C (amino acids 470–715) is 39% and 35% identical to those of GC-A and GC-B, respectively (GC-A and GC-B are 72% identical within this domain). The GXGXXG consensus sequence found in protein kinases (GXGSSSG in GC-A and LXGSSSG in GC-B) is absent in GC-C (25). Across the catalytic domain (amino acids 737–1006) GC-C is 55% identical to GC-A and GC-B, whereas the natriuretic peptide receptors are almost identical with each other within this domain (91%).

Expression of GC-C in Mammalian Cells

GC-C, in the mammalian expression vector pSVL (pSVL-C), was transiently expressed in COS-7 cells. Transfected cells were assayed for guanylyl cyclase activity, accumulation of cyclic GMP in response to STa (an 18 amino acid heat-stable enterotoxin produced by E. coli) or natriuretic peptides, and $^{125}$I-STa binding. Membranes prepared from pSVL-C transfected cells expressed markedly increased guanylyl cyclase activity as compared to membranes prepared from vector transfected cells (Table 1). Virtually all enzyme activity was solubilized by non-ionic detergent.

Figure 4:
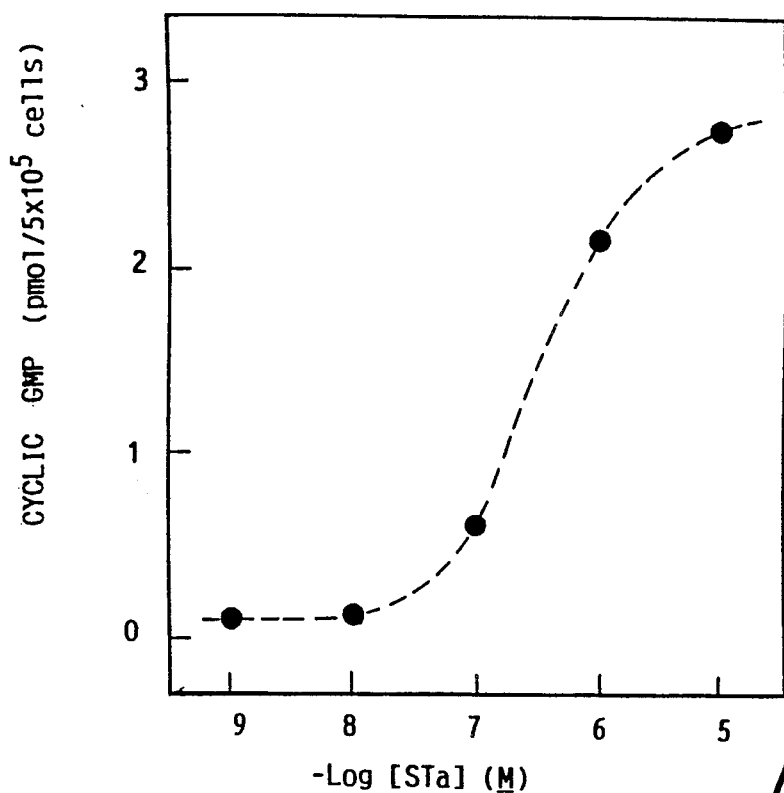
FIG. 4 is a graph plotting cyclic GMP versus-log [STa] (M) showing STa dependent accumulation of cyclic GMP in transfected cells.

Exposure of intact pSVL-C transfected cells to STa resulted in a concentration-dependent accumulation of intracellular cyclic GMP (FIG. 4), with a half-maximal response at 300 nM Sta, as shown in FIG. 4. Half-maximal effects of STa on cyclic GMP concentrations reported for human $T_{84}$ colonic cells or for opossum kidney cells have been in the 100 nM range, with maximal effects normally seen at about 1 uM STa (26,27). Stimulation of transfected cells with atrial, brain or C-type natriuretic peptide did not increase cyclic GMP levels above background (data not shown). The response to STa was specific to pSVL-C transfected cells. Cells transfected with pSVL vector alone or with pSVL containing GC-A or GC-B showed no accumulation of cyclic GMP in response to STa as shown in Table 2.

Figure 5:
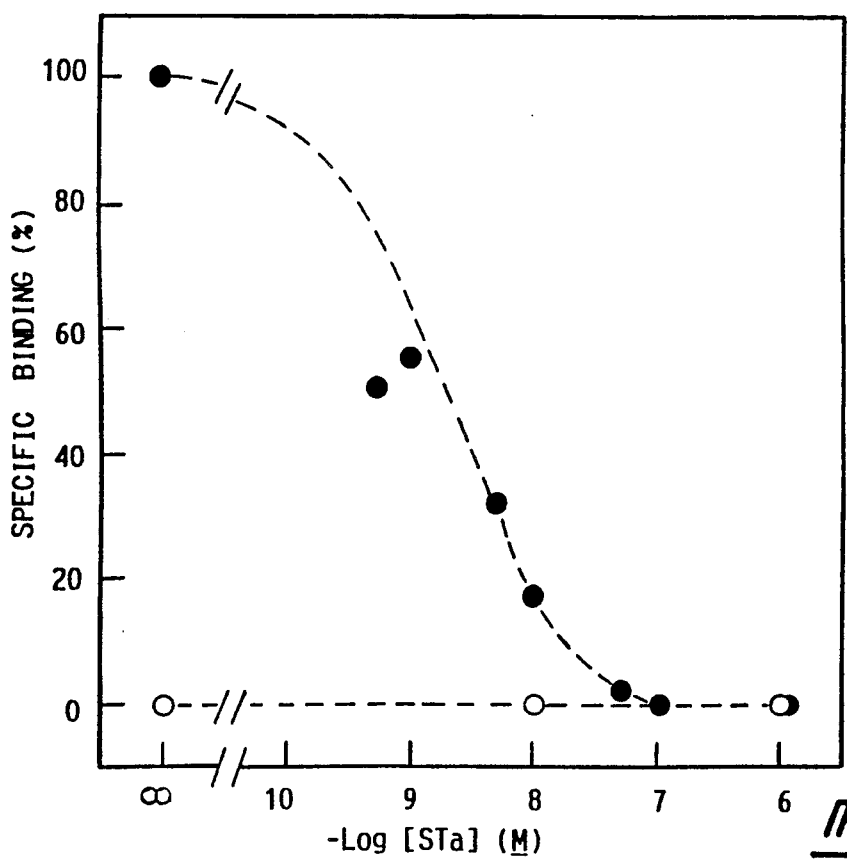
FIG. 5 is a graph showing percent specific bound versus -log [STa] (M) showing specific $^{125}$I-STa binding to transfected cells.

FIG. 5 shows the results of a representative competition binding assay. pSVL-C transfected cells specifically bound $^{125}$I-STa and unlabeled STa effectively competed for binding. Vector transfected cells showed no specific binding.

The above results show that applicant has cloned and sequenced a protein and the nucleotides encoding the protein which has a biological property of binding heat stable enterotoxin having guanylyl cyclase activity. The protein contains a single putative transmembrane domain and an intracellular portion including a protein kinase domain and a cyclase catalytic domain. The protein is derived from the clone designaed as PSVL-GCC having an ATCC deposit number 68482.

Unlike the two previously isolated mammalian plasma membrane forms of guanylyl cyclase, the form isolated in accordance with the present invention binds heat stable enterotoxin.

The predicted primary structure of GC-C bears virtually no resemblance to the other guanylyl cyclases, GC-A or GC-B in the putative extracellular domain. Atrial, brain and C- type natriuretic peptide failed to stimulate GC-C even at micromolar concentration and likewise, ST fails to effect GC-A or GC-B activity. Accordingly, it can be concluded that GC-C is a novel cyclase, uniquely having the capacity to bind heat stable enterotoxin.

All of the cell surface forms of guanylyl cyclase previously isolated, possessed both a protein kinase like domain and a cyclase catalytic domain within intracellular regions. The primary sequence within the cyclase catalytic domain is the most highly conserved region, being approximately 46% and 55% identical between GC-C and the sea urchin guanylyl cyclase and the natriuretic peptides/guanylyl cyclase receptors, respectively. The protein kinase domain of GC-C appears to diverge considerably from GC-A and GC-B, being only 39% and 35% identical, respectively.

Since the present invention now provides means for over-producing GC-C (that is, expressing GC-C from cells at levels not before expressed in cells or even expressing in cells not previously having the capability of expressing GC-C) applicant now possesses a very sensitive assay for ligands naturally binding the isolated novel receptor. The identification of such a ligand would provide a major step in defining the normal function of the receptor. Moreover, the action of ST appears to be explained by their interaction with the single receptor isolated by the present invention.

In view of the above, applicant has cloned the mRNA for the intestinal receptor which recognizes heat stable enterotoxins and have deduced the protein sequence thereof. This protein has been expressed in cultured cells and has been shown to bind enterotoxin and further signal normally through the cyclic GMP second messenger system. The clone and the expressed protein can be used in the treatment of diarrhea in various ways.

For example, pursuant to known techniques(:) polyclonal antibodies to the extracellular domain, site-specific antibodies to synthetic peptides, and monoclonal antibodies to the extracellular domain can be produced which interact with the enterotoxin binding site (28). The antibody can be made against the protein or polypeptide corresponding to the binding domain of the protein to block toxin binding, thereby eliminating the toxins effect in vivo. Additionally, delivery of the binding domain of the receptor protein to the intestine can compete with intestinal receptor for enterotoxin, thereby decreasing or eliminating diarrhea. Further, since the clone has been expressed, it is possible that the clone can be expressed in a nonpathogenic, over-producing strain of bacteria, such as E. coli, which will result in larger amounts of competing toxin receptor in order to therapeutically eliminate diarrhea. Finally, binding studies discussed above demonstrate the ability of the present invention to be used as a method to rapidly screen for antagonists of toxin binding, using competition for the $^{125}$I-ST binding or inhibition of stimulation of cyclic GMP production as an assay.

The invention has been described in an illustrative manner, and it is to be understood that the terminology which has been used is intended to be in the nature of words of description rather than of limitation.

Obviously, many modifications and variations of the present invention are possible in light of the above teachings. It is, therefore, to be understood that within the scope of the appended claims the invention may be practiced otherwise than as specifically described.

TABLE 1

Guanylyl Cylcase Activity Associated with Transfected Cell Membranes

| Transfected DNA | | Guanylyl Cyclase Activity (pmol cyclic GMP formed/mg protein) |
|---|---|---|
| pSVL | detergent-insoluble | 48 |
|  | detergent-soluble | 6 |
| pSVL-C | detergent-insoluble | 21 |
|  | detergent-soluble | 455 |

Membranes were prepared from COS-7 cells transfected with pSVL (no insert) or pSVL-C (GC-C). Enzyme activity was then determined in the Triton X-100-soluble and -insoluble fractions. Triplicate samples were incubated for 10 min at 30° C.

TABLE 2

| Accumulation of Cyclic GMP in Response to STa | |
|---|---|
| Transfected DNA | pmol Cyclic GMP/5 × $10^5$ cells |
| PSVL | <0.10 |
| pSVL-A | 0.10 |
| pSVL-B | <0.10 |
| pSVL-C | 15.3 |

Intact COS-7 cells transfected with pSVL (no insert), pSVL-A (GC-A), pSVL-B (GC-B) or pSVL-C (GC-C) were exposed to 1 μM STa for 10 min. 0.1 mM IBMX was included in the reaction mixture to inhibit cyclic nucleotide degradation. Cells were extracted with perchloric acid, and cyclic GMP was then quantitated by radioimmunoassay.

REFERENCES

1. Thompson, M. R. (1987) *Escherichia coli* heat-stable enterotoxins and their receptors. Pathol. Immunopathol. Res. 6, 103-116.

2. Giannella, R. A. (1981). Pathogenesis of acute bacterial diarrheal disorders. Ann. Rev. Med. 32, 341-357.

3. Burgess, M. N. et al (1978). Biological evaluation of a methanol soluble, heat-stable enterotoxin in infant mice, pigs, rabbits and calves. Infect. Immun. 21, 526-531.

4. Field, M. et al (1978). Heat-stable enterotoxin of *Escherichia coli:* In vivo effects on guanylate cyclase activity, cyclic GMP concentration, and ion transport in small intestine. Proc. Natl. Acad. Sci. USA 75, 2800-2804.

5. Guerrant, R. L. et al (1980). Activation of intestinal guanylate cyclase by heat-stable enterotoxin of *Escherichia coli:* Studies of tissue specificity, potential receptors, and intermediates. J. Infectios Diseases 142, 220-228.

6. Kuno, T. et al (1986). Characterization of the receptor for heat-stable enterotoxin from *Escherichia coli* in rat intestine. J. Biol. Chem. 261, 1470-1476

7. Waldman, S. A. et al (1986). Intestinal receptor for heat-stable enterotoxin of *Escherichia coli* is tightly coupled to a novel form of particulate guanylate cyclase. Infect. Immun. 51, 320-326.

8. Shimomura, H. et al (1986). Covalent coupling of a resact analogue to guanylate cyclase. J. Biol. Chem. 261, 15778-15782.

9. Garbers, D. L. (1989) Molecular basis of fertilization. Annu. Rev. Biochem. 58, 719-742.

10. Chinkers, M. et al (1989). A membrane form of guanylate cyclase is an atrial natriuretic peptide receptor. Nature 338, 78-83.

11. Lowe, D. G. et al (1989). Human atrial natriuretic peptide receptor defines a new paradigm for second messenger signal transduction. EMBO J. 8, 1377-1384.

12. Chang, M.-S. et al (1989). Differential activation by atrial and brain natriuretic peptides of two different receptor guanyulate cyclases. Nature 341, 68-72.

13. Schultz, S. et al (1989. The primary structure of plasma membrane guanylate cyclase demonstrates diversity within this new receptor family. Cell 58, 1155-1162.

14. Krupinski, J. et al (1989). Adenylyl cyclase amino acid sequence possible channel- or transporter-like structure. Science, 244, 1558-1564.

15. Cathala, G. et al (1983). A method for isolation of intact, translationally active ribonucleic acid. DNA 2, 329-335.

16. Cullen, B. R. (1987). Use of eukaryotic expression technology in the functional analysis of cloned genes. Meth. Enzymol. 152, 684-704.

17. Hansbrough, J. R. et al (1981). Speract: purification and characterization of a peptide associated with eggs that activates spermatoza. J. Biol. Chem. 256, 1447-1452.

18. Thompson, M. R. et al (1985). Biological and immunological characteristics of $^{125}$I-4Tyr and -18Tyr *Escherichia coli* heat-stable enterotoxin species purified by high performance liquid chromatography. Anal. Biochem. 148, 26-36.

19. Sommer, R. et al (1989). Minimal homology requirements for PCR primers. Nucleic Acids Res. 17, 6749.

20. Kozak, M. (1989). The scanning model for translation: an update. J. Cell Biol. 108, 229-241.

21. von Heijne, G. (1983). Patterns of amino acids near signal-sequence cleavage sites. Eur. J. biochem. 133, 17-21.

22. Chinkers, M. et al (1989). The protein kinase domain of the ANP receptor is required for signaling. Science 245, 1392-1394.

23. Singh, S. et al (1988). Membrane guanylate cyclase is a cell-surface receptor with homology to protein kinases. Nature 334, 708-712.

24. Thorpe, D. S. et al (1989). The membrane form of guanylate cyclase: homology with a subunit of the cytoplasmic form of the enzyme. J. Biol. Chem. 264, 6545-6549.

25. Hanks, S. K. et al (1988). The protein kinase family: conserved features and deduced phylogeny of the catalytic domains. Science 241, 42-52.

26. Huott, F. A. et al (1988). Mechanism of action of *Escherichia coli* heat stable enterotoxin in a human colonic cell line. J. Clin. Invest. 82, 514-523.

27. White, A. A. et al (1989). Opossum kidney contains a functional receptor for the *Escherichia coli* heat-stable enterotoxin. Biochem. Biophys. Res. Commun. 59, 363-367.

28. Harlow, E. et al (1989). Antibodies. A Laboratory Manual. Cold Spring Harbor Laoratory. New York. pp. 1-726.

---

What is claimed is:

1. A purified, isolated protein having a biological property of binding heat stable enterotoxin and having guanylyl cyclase activity, said protein containing a single putative transmembrane domain and an intracellular portion including a protein kinase domain and a cyclase catalytic domain, said protein derived from a clone PSVL-GCC having ATCC Deposit No. 68482.

2. A purified, isolated protein having a biological property of binding heat stable enterotoxin and having guanylyl cyclase activity, said protein containing a single putative transmembrane domain and an intracellular portion including a protein kinase domain and a cyclase catalytic domain, said protein having an amino acid sequence as shown in FIG. 1 (SEQ ID NO 2) or which is encoded for by a DNA which is capable of hybridizing to a DNA encoding the amino acid sequence shown in FIG. 1 (SEQ ID NO 2) under moderately stringent washing conditions.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:
        ( A ) LENGTH: 3784 base pairs
        ( B ) TYPE: nucleic acid
        ( C ) STRANDEDNESS: double
        ( D ) TOPOLOGY: linear ( i i ) MOLECULE TYPE: cDNA to mRNA ( v i i ) IMMEDIATE SOURCE:
        ( A ) LIBRARY: gt11 cDNA
        ( B ) CLONE: #Microsoft Corp ( i x ) FEATURE:
        ( A ) NAME/KEY: CDS
        ( B ) LOCATION: 11..3235

( i x ) FEATURE:
        ( A ) NAME/KEY: sigpeptide
        ( B ) LOCATION: 11..76

-continued (ix) FEATURE:
    (A) NAME/KEY: transitpeptide
    (B) LOCATION: 1298..1369

(ix) FEATURE:
    (A) NAME/KEY: 5'clip
    (B) LOCATION: 1..10

(ix) FEATURE:
    (A) NAME/KEY: 3'UTR
    (B) LOCATION: 3236..3784

(xi) SEQUENCE DESCRIPTION: SEQ ID NO:1:

```
GAGCGAGGTC ATG ACG TCA CTC CTG GGC TTG GCT GTG CGG TTA CTG CTC         49
           Met Thr Ser Leu Leu Gly Leu Ala Val Arg Leu Leu Leu
           1               5                   10

TTC CAA CCC ACG CTG ATG TTC TGG GCC TCC CAG GTG AGG CAG AAG TGC        97
Phe Gln Pro Thr Leu Met Phe Trp Ala Ser Gln Val Arg Gln Lys Cys
            15                  20                  25

CAC AAT GGC ACC TAC GAG ATC AGT GTC CTG ATG ATG GAT AAC TCA GCC       145
His Asn Gly Thr Tyr Glu Ile Ser Val Leu Met Met Asp Asn Ser Ala
30                  35                  40                  45

TAC AAA GAA CCT TTG CAA AAC TTG AGG GAT GCT GTG GAG GAA GGA CTG       193
Tyr Lys Glu Pro Leu Gln Asn Leu Arg Asp Ala Val Glu Glu Gly Leu
                50                  55                  60

GAC ATC GTG CGA AAG GCC CTG CGC GAA GCC GAA CTA AAT GTG ACT GTG       241
Asp Ile Val Arg Lys Ala Leu Arg Glu Ala Glu Leu Asn Val Thr Val
            65                  70                  75

AAC GCA ACC TTC ATC TAC TCC GAT GGT CTG ATC CAT AAG TCA GGT GAC       289
Asn Ala Thr Phe Ile Tyr Ser Asp Gly Leu Ile His Lys Ser Gly Asp
        80                  85                  90

TGC CGG AGC AGT ACC TGT GAA GGC CTT GAC CTC CTC AGG GAA ATT ACA       337
Cys Arg Ser Ser Thr Cys Glu Gly Leu Asp Leu Leu Arg Glu Ile Thr
    95                  100                 105

AGA GAT CGT AAG ATG GGC TGT GTC CTC ATG GGG CCC TCG TGC ACG TAT       385
Arg Asp Arg Lys Met Gly Cys Val Leu Met Gly Pro Ser Cys Thr Tyr
110                 115                 120                 125

TCC ACC TTC CAG ATG TAC CTT GAC ACA GAG TTG AAC TAT CCC ATG ATT       433
Ser Thr Phe Gln Met Tyr Leu Asp Thr Glu Leu Asn Tyr Pro Met Ile
                130                 135                 140

TCC GCT GGA AGT TTT GGA TTG TCC TGT GAC TAT AAG GAA ACC CTA ACC       481
Ser Ala Gly Ser Phe Gly Leu Ser Cys Asp Tyr Lys Glu Thr Leu Thr
            145                 150                 155

AGG ATC CTG CCT CCA GCC AGG AAG CTG ATG TAC TTC TTG GTC GAT TTC       529
Arg Ile Leu Pro Pro Ala Arg Lys Leu Met Tyr Phe Leu Val Asp Phe
        160                 165                 170

TGG AAA GTC AAC AAT GCA CCT TTC AAA ACC TTT TCC TGG AAC TCT TCA       577
Trp Lys Val Asn Asn Ala Pro Phe Lys Thr Phe Ser Trp Asn Ser Ser
175                 180                 185

TAT GTT TAC AAG AAC GGA TCG GAG CCT GAA GAT TGT TTC TGG TAC CTC       625
Tyr Val Tyr Lys Asn Gly Ser Glu Pro Glu Asp Cys Phe Trp Tyr Leu
190                 195                 200                 205

AAC GCT CTA GAG GCT GGG GTG TCC TAT TTT TCT GAG GTG CTC AGC TTC       673
Asn Ala Leu Glu Ala Gly Val Ser Tyr Phe Ser Glu Val Leu Ser Phe
                210                 215                 220

AAG GAT GTA TTG AGA CGC AGT GAA CAG TTC CAG GAA ATC CTA ATG GGC       721
Lys Asp Val Leu Arg Arg Ser Glu Gln Phe Gln Glu Ile Leu Met Gly
            225                 230                 235

CGT AAC AGG AAG AGC AAT GTG ATT GTT ATG TGT GGC ACG CCA GAA ACC       769
Arg Asn Arg Lys Ser Asn Val Ile Val Met Cys Gly Thr Pro Glu Thr
        240                 245                 250

TTC TAC AAT GTG AAA GGT GAC CTC AAA GTG GCT GAC GAC ACT GTT GTC       817
Phe Tyr Asn Val Lys Gly Asp Leu Lys Val Ala Asp Asp Thr Val Val
255                 260                 265
```

-continued

| | | | | | | | | | | | | | | | | |
|---|---|---|---|---|---|---|---|---|---|---|---|---|---|---|---|---|
| ATC | CTG | GTA | GAT | CTG | TTC | AGT | AAC | CAT | TAC | TTT | GAG | GAT | GAC | ACC | AGA | 865 |
| Ile 270 | Leu | Val | Asp | Leu 275 | Phe | Ser | Asn | His | Tyr 280 | Phe | Glu | Asp | Asp | Thr | Arg 285 | |
| GCT | CCT | GAG | TAT | ATG | GAC | AAT | GTC | CTC | GTC | CTG | ACA | CTG | CCT | CCT | GAA | 913 |
| Ala | Pro | Glu | Tyr | Met 290 | Asp | Asn | Val | Leu | Val 295 | Leu | Thr | Leu | Pro | Pro 300 | Glu | |
| AAG | TTC | ATC | GCG | AAC | GCC | TCT | GTC | TCT | GGG | AGG | TTT | CCA | TCG | GAA | AGA | 961 |
| Lys | Phe | Ile | Ala 305 | Asn | Ala | Ser | Val | Ser 310 | Gly | Arg | Phe | Pro | Ser 315 | Glu | Arg | |
| AGC | GAC | TTT | TCT | CTC | GCT | TAC | TTG | GAG | GGG | ACC | TTG | CTG | TTT | GGA | CAC | 1009 |
| Ser | Asp | Phe 320 | Ser | Leu | Ala | Tyr | Leu 325 | Glu | Gly | Thr | Leu | Leu 330 | Phe | Gly | His | |
| ATG | CTG | CAG | ACG | TTT | CTT | GAA | AAT | GGA | GAA | TCT | GTC | ACC | ACG | CCC | AAG | 1057 |
| Met | Leu 335 | Gln | Thr | Phe | Leu | Glu 340 | Asn | Gly | Glu | Ser | Val 345 | Thr | Thr | Pro | Lys | |
| TTC | GCT | CGT | GCG | TTC | AGG | AAT | CTC | ACT | TTT | CAA | GGC | TTA | GAG | GGG | CCC | 1105 |
| Phe 350 | Ala | Arg | Ala | Phe | Arg 355 | Asn | Leu | Thr | Phe | Gln 360 | Gly | Leu | Glu | Gly | Pro 365 | |
| GTG | ACT | CTG | GAT | GAC | AGT | GGG | GAC | ATT | GAC | AAC | ATT | ATG | TGT | CTT | CTG | 1153 |
| Val | Thr | Leu | Asp | Asp 370 | Ser | Gly | Asp | Ile | Asp 375 | Asn | Ile | Met | Cys | Leu 380 | Leu | |
| TAT | GTG | TCT | CTG | GAT | ACC | AGG | AAA | TAC | AAG | GTT | CTT | ATG | GCG | TAT | GAC | 1201 |
| Tyr | Val | Ser | Leu 385 | Asp | Thr | Arg | Lys | Tyr 390 | Lys | Val | Leu | Met | Ala 395 | Tyr | Asp | |
| ACC | CAT | AAA | AAC | CAA | ACG | ATC | CCT | GTG | GCT | ACG | AGC | CCC | AAC | TTC | ATC | 1249 |
| Thr | His | Lys 400 | Asn | Gln | Thr | Ile | Pro 405 | Val | Ala | Thr | Ser | Pro 410 | Asn | Phe | Ile | |
| TGG | AAG | AAC | CAC | AGA | CTC | CCT | AAT | GAC | GTT | CCT | GGG | CTG | GGC | CCT | CAA | 1297 |
| Trp | Lys 415 | Asn | His | Arg | Leu | Pro 420 | Asn | Asp | Val | Pro | Gly 425 | Leu | Gly | Pro | Gln | |
| ATC | CTG | ATG | ATT | GCC | GTC | TTC | ACG | CTC | ACG | GGG | ATT | GTG | GTC | GTT | CTG | 1345 |
| Ile | Leu | Met | Ile 430 | Ala | Val | Phe | Thr | Leu 435 | Thr | Gly | Ile | Val | Val 440 | Val | Leu 445 | |
| CTG | CTG | ATT | GCC | CTC | CTT | GTG | CTC | AGA | AAA | TAC | AGA | AGA | GAT | CAT | GAA | 1393 |
| Leu | Leu | Ile | Ala | Leu 450 | Leu | Val | Leu | Arg | Lys 455 | Tyr | Arg | Arg | Asp | His 460 | Glu | |
| CTT | CGA | CAG | AAG | AAA | TGG | TCC | CAC | ATC | CCT | TCT | GAA | AAT | ATC | TTT | CCT | 1441 |
| Leu | Arg | Gln | Lys | Lys 465 | Trp | Ser | His | Ile | Pro 470 | Ser | Glu | Asn | Ile | Phe 475 | Pro | |
| CTG | GAG | ACC | AAC | GAG | ACC | AAC | GAG | ACC | AAC | CAT | GTC | AGC | CTG | AAG | ATT | 1489 |
| Leu | Glu | Thr | Asn | Glu 480 | Thr | Asn | Glu | Thr | Asn 485 | His | Val | Ser | Leu | Lys 490 | Ile | |
| GAC | GAT | GAC | AGG | AGG | CGG | GAT | ACA | ATC | CAG | AGA | GTG | CGA | CAG | TGC | AAA | 1537 |
| Asp | Asp | Asp | Arg 495 | Arg | Arg | Asp | Thr | Ile 500 | Gln | Arg | Val | Arg | Gln 505 | Cys | Lys | |
| TAC | GAC | AAG | AAG | AAA | GTG | ATC | CTG | AAA | GAC | CTC | AAG | CAC | TGT | GAT | GGT | 1585 |
| Tyr | Asp | Lys 510 | Lys | Lys | Val | Ile | Leu 515 | Lys | Asp | Leu | Lys | His 520 | Cys | Asp | Gly 525 | |
| AAC | TTC | AGT | GAG | AAG | CAG | AAG | ATA | GAA | CTG | AAC | AAG | CTA | CTG | CAG | TCA | 1633 |
| Asn | Phe | Ser | Glu | Lys 530 | Gln | Lys | Ile | Glu | Leu 535 | Asn | Lys | Leu | Leu | Gln 540 | Ser | |
| GAC | TAC | TAC | AAC | CTG | ACC | AAG | TTC | TAC | GGC | ACC | GTG | AAG | CTA | GAC | ACC | 1681 |
| Asp | Tyr | Tyr | Asn | Leu 545 | Thr | Lys | Phe | Tyr | Gly 550 | Thr | Val | Lys | Leu | Asp 555 | Thr | |
| AGG | ATC | TTT | GGG | GTG | GTC | GAG | TAC | TGC | GAG | AGG | GGG | TCC | CTC | CGG | GAA | 1729 |
| Arg | Ile | Phe | Gly 560 | Val | Val | Glu | Tyr | Cys 565 | Glu | Arg | Gly | Ser | Leu 570 | Arg | Glu | |
| GTG | TTA | AAT | GAC | ACG | ATT | TCC | TAC | CCT | GAT | GGC | ACG | TTC | ATG | GAT | TGG | 1777 |
| Val | Leu | Asn | Asp | Thr 575 | Ile | Ser | Tyr | Pro | Asp 580 | Gly | Thr | Phe | Met | Asp 585 | Trp | |
| GAG | TTT | AAG | ATC | TCT | GTC | TTA | AAT | GAC | ATT | GCT | AAG | GGG | ATG | TCC | TAT | 1825 |

-continued

| | | | | | | | | | | | | | | | |
|---|---|---|---|---|---|---|---|---|---|---|---|---|---|---|---|
| Glu | Phe | Lys | Ile | Ser | Val | Leu | Asn | Asp | Ile | Ala | Lys | Gly | Met | Ser | Tyr |
| 590 | | | | 595 | | | | | 600 | | | | | 605 | |

| CTG | CAC | TCC | AGT | AAG | ATT | GAA | GTC | CAC | GGG | CGT | CTG | AAG | TCC | ACC | AAC | 1873 |
|---|---|---|---|---|---|---|---|---|---|---|---|---|---|---|---|---|
| Leu | His | Ser | Ser | Lys | Ile | Glu | Val | His | Gly | Arg | Leu | Lys | Ser | Thr | Asn | |
| | | | | 610 | | | | | 615 | | | | | 620 | | |

| TGC | GTG | GTG | GAC | AGT | CGC | ATG | GTG | GTG | AAG | ATC | ACT | GAT | TTT | GGG | TGC | 1921 |
|---|---|---|---|---|---|---|---|---|---|---|---|---|---|---|---|---|
| Cys | Val | Val | Asp | Ser | Arg | Met | Val | Val | Lys | Ile | Thr | Asp | Phe | Gly | Cys | |
| | | | 625 | | | | | 630 | | | | | 635 | | | |

| AAT | TCC | ATC | CTG | CCT | CCA | AAG | AAA | GAC | CTG | TGG | ACT | GCC | CCC | GAG | CAC | 1969 |
|---|---|---|---|---|---|---|---|---|---|---|---|---|---|---|---|---|
| Asn | Ser | Ile | Leu | Pro | Pro | Lys | Lys | Asp | Leu | Trp | Thr | Ala | Pro | Glu | His | |
| | | 640 | | | | 645 | | | | 650 | | | | | | |

| CTG | CGC | CAA | GCT | ACT | ATC | TCT | CAG | AAA | GGA | GAG | CTG | TAC | AGC | TTC | AGC | 2017 |
|---|---|---|---|---|---|---|---|---|---|---|---|---|---|---|---|---|
| Leu | Arg | Gln | Ala | Thr | Ile | Ser | Gln | Lys | Gly | Glu | Leu | Tyr | Ser | Phe | Ser | |
| | 655 | | | | 660 | | | | | 665 | | | | | | |

| ATC | ATT | GCC | CAG | GAG | ATC | ATC | CTC | CGC | AAG | GAA | ACT | TTC | TAC | ACG | CTG | 2065 |
|---|---|---|---|---|---|---|---|---|---|---|---|---|---|---|---|---|
| Ile | Ile | Ala | Gln | Glu | Ile | Ile | Leu | Arg | Lys | Glu | Thr | Phe | Tyr | Thr | Leu | |
| 670 | | | | 675 | | | | | 680 | | | | | 685 | | |

| AGC | TGC | CGG | GAT | CAG | AAT | GAG | AAG | ATT | TTC | AGA | GTG | GAA | AAT | TCC | TAT | 2113 |
|---|---|---|---|---|---|---|---|---|---|---|---|---|---|---|---|---|
| Ser | Cys | Arg | Asp | Gln | Asn | Glu | Lys | Ile | Phe | Arg | Val | Glu | Asn | Ser | Tyr | |
| | | | | 690 | | | | 695 | | | | | 700 | | | |

| GGG | ACG | AAA | CCC | TTC | CGC | CCA | GAT | CTC | TTC | CTG | GAA | ACC | GCA | GAT | GAG | 2161 |
|---|---|---|---|---|---|---|---|---|---|---|---|---|---|---|---|---|
| Gly | Thr | Lys | Pro | Phe | Arg | Pro | Asp | Leu | Phe | Leu | Glu | Thr | Ala | Asp | Glu | |
| | | | 705 | | | | | 710 | | | | | 715 | | | |

| AAG | GAG | CTG | GAG | GTC | TAT | CTA | TTG | GTC | AAA | AGC | TGT | TGG | GAG | GAG | GAT | 2209 |
|---|---|---|---|---|---|---|---|---|---|---|---|---|---|---|---|---|
| Lys | Glu | Leu | Glu | Val | Tyr | Leu | Leu | Val | Lys | Ser | Cys | Trp | Glu | Glu | Asp | |
| | | 720 | | | | | 725 | | | | | 730 | | | | |

| CCA | GAA | AAG | AGA | CCA | GAT | TTC | AAG | AAA | ATC | GAG | AGC | ACA | CTA | GCC | AAG | 2257 |
|---|---|---|---|---|---|---|---|---|---|---|---|---|---|---|---|---|
| Pro | Glu | Lys | Arg | Pro | Asp | Phe | Lys | Lys | Ile | Glu | Ser | Thr | Leu | Ala | Lys | |
| | 735 | | | | 740 | | | | | 745 | | | | | | |

| ATA | TTT | GGC | CTT | TTT | CAT | GAC | CAA | AAA | AAT | GAA | TCT | TAC | ATG | GAC | ACC | 2305 |
|---|---|---|---|---|---|---|---|---|---|---|---|---|---|---|---|---|
| Ile | Phe | Gly | Leu | Phe | His | Asp | Gln | Lys | Asn | Glu | Ser | Tyr | Met | Asp | Thr | |
| 750 | | | | 755 | | | | | 760 | | | | | 765 | | |

| TTG | ATC | CGA | CGT | CTA | CAG | CTG | TAT | TCT | CGG | AAC | CTG | GAG | CAC | CTG | GTG | 2353 |
|---|---|---|---|---|---|---|---|---|---|---|---|---|---|---|---|---|
| Leu | Ile | Arg | Arg | Leu | Gln | Leu | Tyr | Ser | Arg | Asn | Leu | Glu | His | Leu | Val | |
| | | | 770 | | | | | 775 | | | | | 780 | | | |

| GAG | GAA | AGG | ACT | CAG | CTG | TAC | AAG | GCC | GAG | AGG | GAC | AGG | GCT | GAC | CAC | 2401 |
|---|---|---|---|---|---|---|---|---|---|---|---|---|---|---|---|---|
| Glu | Glu | Arg | Thr | Gln | Leu | Tyr | Lys | Ala | Glu | Arg | Asp | Arg | Ala | Asp | His | |
| | | 785 | | | | | 790 | | | | | 795 | | | | |

| CTT | AAC | TTT | ATG | CTG | CTC | CCA | CGG | CTG | GTG | GTA | AAG | TCC | CTG | AAG | GAG | 2449 |
|---|---|---|---|---|---|---|---|---|---|---|---|---|---|---|---|---|
| Leu | Asn | Phe | Met | Leu | Leu | Pro | Arg | Leu | Val | Val | Lys | Ser | Leu | Lys | Glu | |
| | | 800 | | | | | 805 | | | | | 810 | | | | |

| AAA | GGC | ATC | GTG | GAG | CCA | GAG | CTG | TAC | GAA | GAA | GTC | ACA | ATC | TAT | TTC | 2497 |
|---|---|---|---|---|---|---|---|---|---|---|---|---|---|---|---|---|
| Lys | Gly | Ile | Val | Glu | Pro | Glu | Leu | Tyr | Glu | Glu | Val | Thr | Ile | Tyr | Phe | |
| 815 | | | | 820 | | | | | 825 | | | | | | | |

| AGT | GAC | ATT | GTC | GGT | TTC | ACG | ACC | ATC | TGC | AAG | TAC | AGC | ACG | CCC | ATG | 2545 |
|---|---|---|---|---|---|---|---|---|---|---|---|---|---|---|---|---|
| Ser | Asp | Ile | Val | Gly | Phe | Thr | Thr | Ile | Cys | Lys | Tyr | Ser | Thr | Pro | Met | |
| 830 | | | | 835 | | | | 840 | | | | | 845 | | | |

| GAG | GTG | GTG | GAC | ATG | CTG | AAT | GAC | ATC | TAC | AAG | AGT | TTT | GAC | CAG | ATT | 2593 |
|---|---|---|---|---|---|---|---|---|---|---|---|---|---|---|---|---|
| Glu | Val | Val | Asp | Met | Leu | Asn | Asp | Ile | Tyr | Lys | Ser | Phe | Asp | Gln | Ile | |
| | | | | 850 | | | | 855 | | | | | 860 | | | |

| GTG | GAT | CAC | CAC | GAC | GTC | TAC | AAG | GTA | GAA | ACC | ATC | GGC | GAT | GCC | TAC | 2641 |
|---|---|---|---|---|---|---|---|---|---|---|---|---|---|---|---|---|
| Val | Asp | His | His | Asp | Val | Tyr | Lys | Val | Glu | Thr | Ile | Gly | Asp | Ala | Tyr | |
| | | | 865 | | | | 870 | | | | | 875 | | | | |

| GTG | GTG | GCC | AGC | GGC | CTG | CCT | ATG | AGA | AAC | GGC | AAC | CGG | CAT | GCA | GTG | 2689 |
|---|---|---|---|---|---|---|---|---|---|---|---|---|---|---|---|---|
| Val | Val | Ala | Ser | Gly | Leu | Pro | Met | Arg | Asn | Gly | Asn | Arg | His | Ala | Val | |
| | | | 880 | | | | 885 | | | | | 890 | | | | |

| GAC | ATT | TCC | AAG | ATG | GCC | TTG | GAC | ATC | CTC | AGC | TTC | ATG | GGG | ACC | TTT | 2737 |
|---|---|---|---|---|---|---|---|---|---|---|---|---|---|---|---|---|
| Asp | Ile | Ser | Lys | Met | Ala | Leu | Asp | Ile | Leu | Ser | Phe | Met | Gly | Thr | Phe | |
| | | 895 | | | | 900 | | | | | 905 | | | | | |

| GAG | CTG | GAG | CAT | CTC | CCC | GGC | CTC | CCC | GTG | TGG | ATT | CGC | ATT | GGG | GTT | 2785 |
|---|---|---|---|---|---|---|---|---|---|---|---|---|---|---|---|---|
| Glu | Leu | Glu | His | Leu | Pro | Gly | Leu | Pro | Val | Trp | Ile | Arg | Ile | Gly | Val | |
| 910 | | | | 915 | | | | 920 | | | | | 925 | | | |

```
CAT TCT GGC CCC TGT GCT GCT GGT GTG GTG GGG ATC AAG ATG CCT CGT    2833
His Ser Gly Pro Cys Ala Ala Gly Val Val Gly Ile Lys Met Pro Arg
            930                 935                 940

TAT TGC CTG TTT GGA GAC ACT GTC AAC ACT GCC TCC AGG ATG GAG TCC    2881
Tyr Cys Leu Phe Gly Asp Thr Val Asn Thr Ala Ser Arg Met Glu Ser
            945                 950                 955

ACC GGC CTT CCC TTA AGG ATT CAC ATG AGC AGC TCC ACC ATT GCC ATC    2929
Thr Gly Leu Pro Leu Arg Ile His Met Ser Ser Ser Thr Ile Ala Ile
            960                 965                 970

CTG AGG AGA ACG GAT TGC CAG TTC CTG TAC GAA GTG AGG GGA GAA ACG    2977
Leu Arg Arg Thr Asp Cys Gln Phe Leu Tyr Glu Val Arg Gly Glu Thr
            975                 980                 985

TAC TTA AAG GGA AGA GGG ACC GAG ACC ACA TAC TGG CTG ACT GGG ATG    3025
Tyr Leu Lys Gly Arg Gly Thr Glu Thr Thr Tyr Trp Leu Thr Gly Met
990                 995                 1000                1005

AAG GAC CAA GAG TAC AAC CTG CCA ACC CCA CCA ACA GTG GAG AAC CAA    3073
Lys Asp Gln Glu Tyr Asn Leu Pro Thr Pro Pro Thr Val Glu Asn Gln
                1010                1015                1020

CAG CGT CTG CAA ACT GAG TTC TCA GAC ATG ATC GTT AGT GCC TTA CAG    3121
Gln Arg Leu Gln Thr Glu Phe Ser Asp Met Ile Val Ser Ala Leu Gln
                1025                1030                1035

AAA AGA CAG GCC TCG GGC GTG AAG AGC CGG AGG CCC ACT CGG GTG GCC    3169
Lys Arg Gln Ala Ser Gly Val Lys Ser Arg Arg Pro Thr Arg Val Ala
                1040                1045                1050

AGC TAC AAG AAA GGC TTT TTG GAA TAC ATG CAG CTG AAC AAC TCA GAC    3217
Ser Tyr Lys Lys Gly Phe Leu Glu Tyr Met Gln Leu Asn Asn Ser Asp
                1055                1060                1065

CAC GAT AGC ACC TAT TTT TAGACCACGT GCGGTCTAAG AACTGACAGT           3265
His Asp Ser Thr Tyr Phe
1070                1075

AGCAACCTCT GATATCCTGA ATCTGCATTT TCCCAGAAAC CTCAACAACA CAGACAAGTG  3325

CTTAGCCCCA GTGCCCTGTC TGGAATGTAG AACCAGCCCC CAAGTCATGT GGGTGTTCTG  3385

GGTTGGGTTG GGTTGGGTTT GGTTGGTTGG TTTTGTTTCT ATTGAGACAG AGTCTCATGT  3445

ATCCCAAACT GGCCTCAAAC TCGCTGAGGA GCTATGGATG ACCTTGGACT TCTAAGACCA  3505

TCCATGTGTG TTCCTGGCTG TGTGATGCCC TGTCCAGAGT CGTGTCCCAC AGTTCTCCAC  3565

GGAGCATCAA CGTCAGCCTG AAGGGAGGAA GGAGGAACGT ACTATACAGA ACTTGGGGTT  3625

TCATTCTAAT TTCATTTCTG CTTTTTTTCA TTTTGTTTAC TGGATCCTTC CTTATGTACA  3685

CATGAATTTT TTTAATTGTC TGGATTAAGT AGCTTATCTC CAAGAAGTG TGTTTAACTA   3745

GTGATTTTTG CAGAAACCAT GCTGGATATT AGGTAAAAA                         3784
```

( 2 ) INFORMATION FOR SEQ ID NO:2:

( i ) SEQUENCE CHARACTERISTICS:
        ( A ) LENGTH: 1075 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met Thr Ser Leu Leu Gly Leu Ala Val Arg Leu Leu Leu Phe Gln Pro
1               5                   10                  15

Thr Leu Met Phe Trp Ala Ser Gln Val Arg Gln Lys Cys His Asn Gly
                20                  25                  30

Thr Tyr Glu Ile Ser Val Leu Met Met Asp Asn Ser Ala Tyr Lys Glu
            35                  40                  45

Pro Leu Gln Asn Leu Arg Asp Ala Val Glu Glu Gly Leu Asp Ile Val
        50                  55                  60
```

| | | | | | | | | | | | | | | | |
|---|---|---|---|---|---|---|---|---|---|---|---|---|---|---|---|
|Arg|Lys|Ala|Leu|Arg|Glu|Ala|Glu|Leu|Asn|Val|Thr|Val|Asn|Ala|Thr|
|65| | | |70| | | |75| | | |  | | |80|
|Phe|Ile|Tyr|Ser|Asp|Gly|Leu|Ile|His|Lys|Ser|Gly|Asp|Cys|Arg|Ser|
| | | | |85| | | |90| | | |  |  |95| |
|Ser|Thr|Cys|Glu|Gly|Leu|Asp|Leu|Leu|Arg|Glu|Ile|Thr|Arg|Asp|Arg|
| | | |100| | | |105| | | |  |110| |  |  |
|Lys|Met|Gly|Cys|Val|Leu|Met|Gly|Pro|Ser|Cys|Thr|Tyr|Ser|Thr|Phe|
| | |115| | | |120| | | |  |125|  |  |  |  |
|Gln|Met|Tyr|Leu|Asp|Thr|Glu|Leu|Asn|Tyr|Pro|Met|Ile|Ser|Ala|Gly|
| |130| | | |135| | | |  |140|  |  |  |  |  |
|Ser|Phe|Gly|Leu|Ser|Cys|Asp|Tyr|Lys|Glu|Thr|Leu|Thr|Arg|Ile|Leu|
|145| | | |150| | | |155| | |  |  |  |  |160|
|Pro|Pro|Ala|Arg|Lys|Leu|Met|Tyr|Phe|Leu|Val|Asp|Phe|Trp|Lys|Val|
| | | |165| | | |170| | | |  |  |  |175| |
|Asn|Asn|Ala|Pro|Phe|Lys|Thr|Phe|Ser|Trp|Asn|Ser|Ser|Tyr|Val|Tyr|
| | |180| | | | |185| | | |  |  |190| | |
|Lys|Asn|Gly|Ser|Glu|Pro|Glu|Asp|Cys|Phe|Trp|Tyr|Leu|Asn|Ala|Leu|
| |195| | | |200| | | |  |205| |  |  |  |  |
|Glu|Ala|Gly|Val|Ser|Tyr|Phe|Ser|Glu|Val|Leu|Ser|Phe|Lys|Asp|Val|
| |210| | | |215| | | |220| | |  |  |  |  |
|Leu|Arg|Arg|Ser|Glu|Gln|Phe|Gln|Glu|Ile|Leu|Met|Gly|Arg|Asn|Arg|
|225| | | |230| | | |235| | | |  |  |  |240|
|Lys|Ser|Asn|Val|Ile|Val|Met|Cys|Gly|Thr|Pro|Glu|Thr|Phe|Tyr|Asn|
| | | |245| | | |250| | | |  |255| |  |  |
|Val|Lys|Gly|Asp|Leu|Lys|Val|Ala|Asp|Asp|Thr|Val|Val|Ile|Leu|Val|
| | |260| | | |265| | | |  |270|  |  |  |  |
|Asp|Leu|Phe|Ser|Asn|His|Tyr|Phe|Glu|Asp|Asp|Thr|Arg|Ala|Pro|Glu|
| |275| | | |280| | | |285| | |  |  |  |  |
|Tyr|Met|Asp|Asn|Val|Leu|Val|Leu|Thr|Leu|Pro|Pro|Glu|Lys|Phe|Ile|
|290| | | |295| | | |300| | | |  |  |  |  |
|Ala|Asn|Ala|Ser|Val|Ser|Gly|Arg|Phe|Pro|Ser|Glu|Arg|Ser|Asp|Phe|
|305| | | |310| | | |315| | | |  |  |  |320|
|Ser|Leu|Ala|Tyr|Leu|Glu|Gly|Thr|Leu|Leu|Phe|Gly|His|Met|Leu|Gln|
| | | |325| | | |330| | | |  |335| |  |  |
|Thr|Phe|Leu|Glu|Asn|Gly|Glu|Ser|Val|Thr|Thr|Pro|Lys|Phe|Ala|Arg|
| | |340| | | |345| | | |  |350|  |  |  |  |
|Ala|Phe|Arg|Asn|Leu|Thr|Phe|Gln|Gly|Leu|Glu|Gly|Pro|Val|Thr|Leu|
| |355| | | |360| | | |365| | |  |  |  |  |
|Asp|Asp|Ser|Gly|Asp|Ile|Asp|Asn|Ile|Met|Cys|Leu|Leu|Tyr|Val|Ser|
|370| | | |375| | | |380| | | |  |  |  |  |
|Leu|Asp|Thr|Arg|Lys|Tyr|Lys|Val|Leu|Met|Ala|Tyr|Asp|Thr|His|Lys|
|385| | | |390| | | |395| | | |  |  |  |400|
|Asn|Gln|Thr|Ile|Pro|Val|Ala|Thr|Ser|Pro|Asn|Phe|Ile|Trp|Lys|Asn|
| | | |405| | | |410| | | |  |415| |  |  |
|His|Arg|Leu|Pro|Asn|Asp|Val|Pro|Gly|Leu|Gly|Pro|Gln|Ile|Leu|Met|
| | |420| | | |425| | | |  |430|  |  |  |  |
|Ile|Ala|Val|Phe|Thr|Leu|Thr|Gly|Ile|Val|Val|Val|Leu|Leu|Leu|Ile|
| |435| | | |440| | | |445| | |  |  |  |  |
|Ala|Leu|Leu|Val|Leu|Arg|Lys|Tyr|Arg|Arg|Asp|His|Glu|Leu|Arg|Gln|
|450| | | |455| | | |460| | | |  |  |  |  |
|Lys|Lys|Trp|Ser|His|Ile|Pro|Ser|Glu|Asn|Ile|Phe|Pro|Leu|Glu|Thr|
|465| | | |470| | | |475| | | |  |480| |  |  |
|Asn|Glu|Thr|Asn|Glu|Thr|Asn|His|Val|Ser|Leu|Lys|Ile|Asp|Asp|Asp|
| | | |485| | | |490| | | |  |495| |  |  |

-continued

| | | | | | | | | | | | | | | |
|---|---|---|---|---|---|---|---|---|---|---|---|---|---|---|
|Arg|Arg|Arg|Asp 500|Thr|Ile|Gln|Arg 505|Val|Arg|Gln|Cys|Lys 510|Tyr|Asp|Lys|
|Lys|Lys|Val 515|Ile|Leu|Lys|Asp 520|Leu|Lys|His|Cys|Asp 525|Gly|Asn|Phe|Ser|
|Glu 530|Lys|Gln|Lys|Ile|Glu 535|Leu|Asn|Lys|Leu|Leu 540|Gln|Ser|Asp|Tyr|Tyr|
|Asn 545|Leu|Thr|Lys|Phe|Tyr 550|Gly|Thr|Val|Lys|Leu 555|Asp|Thr|Arg|Ile|Phe 560|
|Gly|Val|Val|Glu|Tyr 565|Cys|Glu|Arg|Gly|Ser 570|Leu|Arg|Glu|Val|Leu 575|Asn|
|Asp|Thr|Ile|Ser 580|Tyr|Pro|Asp|Gly|Thr 585|Phe|Met|Asp|Trp|Glu 590|Phe|Lys|
|Ile|Ser|Val 595|Leu|Asn|Asp|Ile|Ala 600|Lys|Gly|Met|Ser|Tyr 605|Leu|His|Ser|
|Ser|Lys 610|Ile|Glu|Val|His|Gly 615|Arg|Leu|Lys|Ser|Thr 620|Asn|Cys|Val|Val|
|Asp 625|Ser|Arg|Met|Val|Val 630|Lys|Ile|Thr|Asp|Phe 635|Gly|Cys|Asn|Ser|Ile 640|
|Leu|Pro|Pro|Lys|Lys 645|Asp|Leu|Trp|Thr|Ala 650|Pro|Glu|His|Leu|Arg 655|Gln|
|Ala|Thr|Ile|Ser 660|Gln|Lys|Gly|Glu|Leu 665|Tyr|Ser|Phe|Ser|Ile 670|Ile|Ala|
|Gln|Glu|Ile 675|Ile|Leu|Arg|Lys|Glu 680|Thr|Phe|Tyr|Thr|Leu 685|Ser|Cys|Arg|
|Asp|Gln|Asn|Glu 690|Lys|Ile|Phe 695|Arg|Val|Glu|Asn|Ser 700|Tyr|Gly|Thr|Lys|
|Pro 705|Phe|Arg|Pro|Asp|Leu 710|Phe|Leu|Glu|Thr|Ala 715|Asp|Glu|Lys|Glu|Leu 720|
|Glu|Val|Tyr|Leu|Leu 725|Val|Lys|Ser|Cys|Trp 730|Glu|Glu|Asp|Pro|Glu 735|Lys|
|Arg|Pro|Asp|Phe 740|Lys|Lys|Ile|Glu|Ser 745|Thr|Leu|Ala|Lys|Ile 750|Phe|Gly|
|Leu|Phe|His 755|Asp|Gln|Lys|Asn|Glu 760|Ser|Tyr|Met|Asp|Thr 765|Leu|Ile|Arg|
|Arg 770|Leu|Gln|Leu|Tyr|Ser 775|Arg|Asn|Leu|Glu|His 780|Leu|Val|Glu|Glu|Arg|
|Thr 785|Gln|Leu|Tyr|Lys|Ala 790|Glu|Arg|Asp|Arg|Ala 795|Asp|His|Leu|Asn|Phe 800|
|Met|Leu|Leu|Pro|Arg 805|Leu|Val|Val|Lys|Ser 810|Leu|Lys|Glu|Lys|Gly 815|Ile|
|Val|Glu|Pro|Glu 820|Leu|Tyr|Glu|Glu|Val 825|Thr|Ile|Tyr|Phe|Ser 830|Asp|Ile|
|Val|Gly|Phe 835|Thr|Thr|Ile|Cys|Lys 840|Tyr|Ser|Thr|Pro|Met 845|Glu|Val|Val|
|Asp|Met 850|Leu|Asn|Asp|Ile|Tyr 855|Lys|Ser|Phe|Asp|Gln 860|Ile|Val|Asp|His|
|His 865|Asp|Val|Tyr|Lys|Val 870|Glu|Thr|Ile|Gly|Asp 875|Ala|Tyr|Val|Val|Ala 880|
|Ser|Gly|Leu|Pro|Met 885|Arg|Asn|Gly|Asn|Arg 890|His|Ala|Val|Asp|Ile 895|Ser|
|Lys|Met|Ala|Leu 900|Asp|Ile|Leu|Ser|Phe 905|Met|Gly|Thr|Phe|Glu 910|Leu|Glu|
|His|Leu|Pro 915|Gly|Leu|Pro|Val|Trp 920|Ile|Arg|Ile|Gly|Val 925|His|Ser|Gly|
|Pro|Cys|Ala|Ala|Gly|Val|Val|Gly|Ile|Lys|Met|Pro|Arg|Tyr|Cys|Leu|

|  | 930 |  |  |  | 935 |  |  |  |  | 940 |  |  |  |
|---|---|---|---|---|---|---|---|---|---|---|---|---|---|
| Phe 945 | Gly | Asp | Thr | Val | Asn 950 | Thr | Ala | Ser | Arg | Met 955 | Glu | Ser | Thr | Gly | Leu 960 |
| Pro | Leu | Arg | Ile | His 965 | Met | Ser | Ser | Ser | Thr 970 | Ile | Ala | Ile | Leu | Arg 975 | Arg |
| Thr | Asp | Cys | Gln 980 | Phe | Leu | Tyr | Glu | Val | Arg 985 | Gly | Glu | Thr | Tyr 990 | Leu | Lys |
| Gly | Arg | Gly 995 | Thr | Glu | Thr | Thr | Tyr 1000 | Trp | Leu | Thr | Gly | Met 1005 | Lys | Asp | Gln |
| Glu | Tyr | Asn 1010 | Leu | Pro | Thr | Pro 1015 | Pro | Thr | Val | Glu | Asn 1020 | Gln | Gln | Arg | Leu |
| Gln 1025 | Thr | Glu | Phe | Ser | Asp 1030 | Met | Ile | Val | Ser | Ala 1035 | Leu | Gln | Lys | Arg | Gln 1040 |
| Ala | Ser | Gly | Val | Lys 1045 | Ser | Arg | Arg | Pro | Thr 1050 | Arg | Val | Ala | Ser | Tyr 1055 | Lys |
| Lys | Gly | Phe | Leu 1060 | Glu | Tyr | Met | Gln | Leu 1065 | Asn | Asn | Ser | Asp | His 1070 | Asp | Ser |
| Thr | Tyr | Phe 1075 |